United States Patent
Soneda et al.

(10) Patent No.: US 10,925,848 B2
(45) Date of Patent: Feb. 23, 2021

(54) AMIDE DERIVATIVE

(71) Applicant: Daiichi Sankyo Company, Limited, Tokyo (JP)

(72) Inventors: Tsuyoshi Soneda, Fujisawa (JP); Hiroki Sakai, Takatsuki (JP); Koji Matsumoto, Machida (JP); Naomi Tanaka, Mitaka (JP); Taichi Fukunaga, Shinagawa-ku (JP)

(73) Assignee: Daiichi Sankyo Company, Limited, Tokyo (JP)

(*) Notice: Subject to any disclaimer, the term of this patent is extended or adjusted under 35 U.S.C. 154(b) by 0 days.

(21) Appl. No.: 16/487,401

(22) PCT Filed: Feb. 20, 2018

(86) PCT No.: PCT/JP2018/005852
§ 371 (c)(1),
(2) Date: Aug. 20, 2019

(87) PCT Pub. No.: WO2018/155398
PCT Pub. Date: Aug. 30, 2018

(65) Prior Publication Data
US 2019/0365688 A1 Dec. 5, 2019

(30) Foreign Application Priority Data

Feb. 21, 2017 (JP) .................. 2017-029768

(51) Int. Cl.
*A61P 43/00* (2006.01)
*A61P 13/12* (2006.01)
*A61K 31/198* (2006.01)
*A61K 31/277* (2006.01)
*C07C 237/36* (2006.01)
*C07C 237/44* (2006.01)

(52) U.S. Cl.
CPC .......... *A61K 31/198* (2013.01); *A61K 31/277* (2013.01); *A61P 13/12* (2018.01)

(58) Field of Classification Search
CPC ........ A61P 43/00; A61P 13/12; A61K 31/198; A61K 31/277; C07C 237/36; C07C 237/44
See application file for complete search history.

(56) References Cited

PUBLICATIONS

HeartDiseasePrevention, 2020, https://www.mayoclinic.org/diseases-conditions/heart-disease/in-depth/heart-disease-prevention/art-20046502.*
ChronicKidneyDisease, 2020, https://www.mayoclinic.org/diseases-conditions/chronic-kidney-disease/diagnosis-treatment/drc-20354527.*
Chronic_Kidney_Disease_Prevention, 2020, https://www.webmd.com/a-to-z-guides/understanding-kidney-disease-prevention.*
Roager-et-al, 2018, Nature Communications, 10 pages.*
RN94-16-6, 1984, registry database entry.*
RN319-36-8, 1984, registry database entry.*
Carnmalm, B., et al., "Potential X-Ray Contrast Agents: IV. Synthesis of α-(acetamidoiodobenzamido) Isobutyric Acids and Some Related Iodinated Compounds," Acta Pharmaceutica Suecica 11(2):167-174, 1974.
Ichii, O., et al., "Podocyte Injury Caused by Indoxyl Sulfate, a Uremic Toxin and Aryl-Hydrocarbon Receptor Ligand," PLOS One 9(9):e108448, Sep. 2014, 15 pages.
Schulman, G., et al., "A Multicenter, Randomized, Double-Blind, Placebo-Controlled, Dose-Ranging Study of AST-120 (Kremezin) in Patients With Moderate to Severe CKD," American Journal of Kidney Diseases 47(4):565-577, Apr. 2006.
Shimizu, H., et al., "Senescence and Dysfunction of Proximal Tubular Cells are Associated With Activated p53 Expression by Indoxyl Sulfate," American Journal of Physiology-Cell Physiology 299(5):C1110-C1117, Nov. 2010.

* cited by examiner

*Primary Examiner* — Sun Jae Yoo
(74) *Attorney, Agent, or Firm* — Christensen O'Connor Johnson Kindness PLLC

(57) ABSTRACT

An object of the present invention is to find a novel pharmaceutical that has an excellent tryptophanase inhibitory effect, and suppresses worsening of renal function to preserve the kidney by reducing production of indoxyl sulfate in the blood. Provided is a pharmaceutical composition containing, as an active ingredient, a compound represented by formula (I) or a pharmacologically acceptable salt thereof. In the formula (I), $R^1$ and $R^2$ are the same or different, and represent a $C_1$-$C_6$ alkyl group, a halogeno $C_1$-$C_6$ alkyl group or a $C_3$-$C_6$ cycloalkyl group; n represents 0, 1 or 2; each X represents a $C_1$-$C_6$ alkyl group, a $C_3$-$C_6$ cycloalkyl group, a halogen atom or the like; and Y represents a hydrogen atom, a $C_1$-$C_6$ alkoxy group, a $C_3$-$C_6$ cycloalkoxy group or a halogeno $C_1$-$C_6$ alkoxy group.

21 Claims, 4 Drawing Sheets

AMIDE DERIVATIVE

TECHNICAL FIELD

The present invention relates to an amide derivative having an excellent tryptophanase inhibitory effect, or a pharmacologically acceptable salt thereof.

BACKGROUND ART

Chronic kidney disease is a significant problem in society. In current drug therapy for chronic kidney disease patients, renin-angiotensin-based inhibitors such as angiotensin II receptor antagonists (ARBs) or angiotensin converting enzyme (ACE) inhibitors are used as a first-line-drug, and calcium antagonists and diuretics are used as second- or third-line-drugs. Based on comorbid diseases and primary diseases, a large number of oral drugs are prescribed, such as therapeutic drugs for hyperuricemia, therapeutic drugs for hyperlipidemia, therapeutic drugs for diabetes, steroid/immunosuppressive agents, antiplatelet drugs/anticoagulation drugs, therapeutic drugs for hyperphosphatemia, erythropoiesis stimulating factor preparations, analgesics, antiarrhythmic drugs, antidepressants, therapeutic drugs for Alzheimer type dementia, Parkinson's disease drugs, proton pump inhibitors (PPI), antiallergic drugs and antimicrobials. There is, however, a demand for development of better therapeutic drugs for these diseases.

Indole, which is produced by tryptophanase-expressing intestinal bacteria with tryptophan used as a substrate, is a precursor of indoxyl sulfate (IS), a uremic toxin which accelerates the progression of chronic kidney disease. Indoxyl sulfate, which is produced from indole through hydroxylation/sulfation, is a uremic toxin that not only deteriorates kidney function and thus accelerates transition to end-stage kidney failure (transition to renal replacement therapy or kidney transplant) but also causes deterioration and dysfunction of blood vessels to cause cardiovascular disease and a further increase in morbidity. Uremic toxins are also deeply involved in disorders of various organs such as nerves, bones, blood cells and skeletal muscles, and uremic symptoms. Spherical adsorptive carbon is commercially available as a pharmaceutical capable of reducing indoxyl sulfate in blood, and adsorbs indole produced by tryptophanase in the lumen of the digestive tract to evacuate it with excrement. The indoxyl sulfate-reducing function of the spherical adsorptive carbon in blood is, however, weak, particularly in humans, and is insufficient because it is unable to reduce blood indoxyl sulfate concentrations down to a concentration level of a healthy subject (Non Patent Literature 1).

Transition to kidney transplant or dialysis because of renal dysfunction is increasing worldwide. For example, the number of dialysis patients in Japan exceeds 310,000 at present and is still increasing. A patient needs to go to hospital three times a week for dialysis, and the dialysis itself takes time. Besides, dialysis is a heavy burden also from the point of view of medical economics. Kidney transplant is also considered as an alternative to dialysis, but the number of donors is limited, and there is therefore a significant problem to be solved preserving renal function as long as possible to support the life of patients. In other words, it has become very important to delay transition to renal replacement therapy in patients with chronic kidney failure at the pre-dialysis stage to gain time until appearance of a donor for kidney transplantation. Besides, after transition to renal replacement therapy, it is important to suppress worsening of residual renal function and to obtain a sufficient urine volume in the sense of water regulation and the like. Indoxyl sulfate accelerates production of ROS (reactive oxygen species) in renal tubular epithelial cells and accelerates cell senescence (Non Patent Literature 2). It is also known to cause damage in renal glomerular epithelial cells via an AhR (aryl hydrocarbon receptor) (Non Patent Literature 3). Therefore, reducing the production of indoxyl sulfate is expected to greatly reduce such influences on renal cells to suppress worsening of renal function and preserve the kidney.

Non Patent Literature 4 describes α-(4-aminobenzamide) isobutyric acid and an iodinated product thereof, but neither discloses nor suggests the tryptophanase inhibitory effect of the present invention.

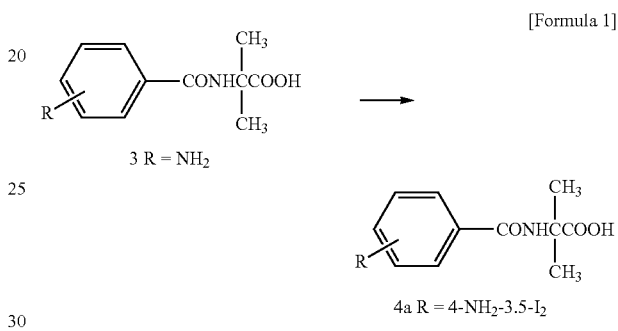

[Formula 1]

In addition, a variety of reagents are commercially available from Aldlab Chemicals, LLC, Aurora Fine Chemicals LLC, SIA "Chemspace" and the like, but medical uses such as the tryptophanase inhibitory effect of the present invention are not known.

CITATION LIST

Non Patent Literature

Non Patent Literature 1: Schulman-G AJKD, Vol. 47, NO 4, 565-576, (2006)
Non Patent Literature 2: Shimizu-H, Am J Physiol Cell Physiol 299: C1110-C1117, 2010
Non Patent Literature 3: Ichii-O, PLOS ONE, 9, e108448, (2014)
Non Patent Literature 4: Acta Pharm. Succica, Vol. 11, 167-174 (1974)

SUMMARY OF INVENTION

Technical Problem

Currently known compounds having a tryptophanase inhibitory effect are not satisfactory in terms of efficacy, and compounds having a tryptophanase inhibitory effect with excellent efficacy have been desired.

Solution to Problem

The present inventors carried out various synthetic studies aiming to provide a novel pharmaceutical that has excellent tryptophanase inhibitory function and suppresses worsening of renal function to preserve a kidney by greatly reducing the indoxyl sulfate concentration in the blood and kidney by inhibiting the production of indole, i.e., a precursor of indoxyl sulfate. As a result, it was found that an amide derivative having a specific structure or a pharmacologically acceptable salt thereof has excellent tryptophanase inhibitory function, and the present invention was thus accomplished.

The present invention provides an amide derivative having excellent tryptophanase inhibitory function or a pharmacologically acceptable salt thereof, and a pharmaceutical composition containing these.

Specifically, the present invention provides the following:

(1) a pharmaceutical composition comprising, as an active ingredient, a compound represented by the following general formula (I) or a pharmacologically acceptable salt thereof:

[Formula 2]

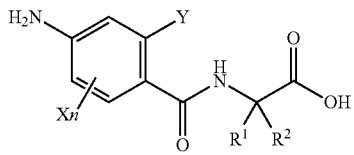

(I)

wherein $R^1$ and $R^2$ are the same or different, and represent a $C_1$-$C_6$ alkyl group, a halogeno $C_1$-$C_6$ alkyl group or a $C_3$-$C_6$ cycloalkyl group; n represents 0, 1 or 2; each X is the same or different, and represents a $C_1$-$C_6$ alkyl group, a $C_3$-$C_6$ cycloalkyl group, a halogen atom, a cyano group, a halogeno $C_1$-$C_6$ alkyl group, a $C_1$-$C_6$ alkoxy group, a halogeno $C_1$-$C_6$ alkoxy group or a $C_3$-$C_6$ cycloalkoxy group; and Y represents a hydrogen atom, a $C_1$-$C_6$ alkoxy group, a $C_3$-$C_6$ cycloalkoxy group or a halogeno $C_1$-$C_6$ alkoxy group;

(2) a compound represented by the following general formula (Ia) or a pharmacologically acceptable salt thereof:

[Formula 3]

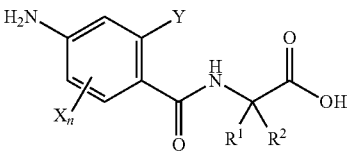

(Ia)

wherein (A) $R^1$ and $R^2$ are the same or different, and represent a $C_1$-$C_6$ alkyl group, a halogeno $C_1$-$C_6$ alkyl group or a $C_3$-$C_6$ cycloalkyl group; n represents 1; X represents a $C_1$-$C_6$ alkyl group, a $C_3$-$C_6$ cycloalkyl group, a halogen atom, a cyano group, a halogeno $C_1$-$C_6$ alkyl group, a $C_1$-$C_6$ alkoxy group, a halogeno $C_1$-$C_6$ alkoxy group or a $C_3$-$C_6$ cycloalkoxy group; and Y represents a $C_1$-$C_6$ alkoxy group, a $C_3$-$C_6$ cycloalkoxy group or a halogeno $C_1$-$C_6$ alkoxy group; or (B) $R^1$ represents an ethyl group; $R^2$ represents a $C_1$-$C_6$ alkyl group, a halogeno $C_1$-$C_6$ alkyl group or a $C_3$-$C_6$ cycloalkyl group; n represents 0, 1 or 2; each X is the same or different, and represents a $C_1$-$C_6$ alkyl group, a $C_3$-$C_6$ cycloalkyl group, a halogen atom, a cyano group, a halogeno $C_1$-$C_6$ alkyl group, a $C_1$-$C_6$ alkoxy group or a halogeno $C_1$-$C_6$ alkoxy group; and Y represents a hydrogen atom, provided that X does not represent a halogen atom or a $C_1$-$C_6$ alkoxy group when $R^2$ represents an ethyl group; and neither X represents a $C_1$-$C_6$ alkoxy group when n represents 2;

(3) the compound according to (2) represented by the following general formula (I-1) or a pharmacologically acceptable salt thereof:

[Formula 4]

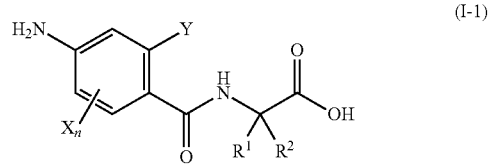

(I-1)

wherein $R^1$ and $R^2$ are the same or different, and represent a $C_1$-$C_4$ alkyl group or a $C_3$-$C_4$ cycloalkyl group; n represents 1; X represents a $C_1$-$C_4$ alkyl group, a $C_3$-$C_4$ cycloalkyl group, a halogen atom, a cyano group or a halogeno $C_1$-$C_4$ alkyl group; and Y represents a $C_1$-$C_4$ alkoxy group or a halogeno $C_1$-$C_4$ alkoxy group;

(4) the compound according to (3) represented by the following general formula (I-1a) or a pharmacologically acceptable salt thereof:

[Formula 5]

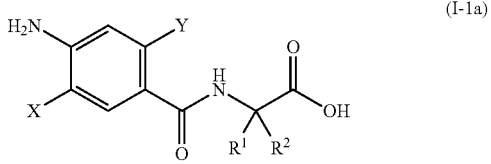

(I-1a)

wherein $R^1$ and $R^2$ are the same or different, and represent a $C_1$-$C_3$ alkyl group or a cyclopropyl group; X represents a $C_1$-$C_3$ alkyl group, a fluorine atom, a chlorine atom, a bromine atom, an iodine atom, a cyano group or a fluoro-$C_1$-$C_3$ alkyl group; and Y represents a $C_1$-$C_3$ alkoxy group or a fluoro-$C_1$-$C_3$ alkoxy group;

(5) the compound according to (4), or a pharmacologically acceptable salt thereof, wherein $R^1$ and $R^2$ are the same or different, and represent a methyl group, an ethyl group, a propyl group or a cyclopropyl group;

(6) the compound according to (4), or a pharmacologically acceptable salt thereof, wherein $R^1$ and $R^2$ are the same or different, and represent a methyl group or an ethyl group;

(7) the compound according to any one of (4) to (6), or a pharmacologically acceptable salt thereof, wherein X represents a fluorine atom, a chlorine atom, a bromine atom or an iodine atom;

(8) the compound according to any one of (4) to (6), or a pharmacologically acceptable salt thereof, wherein X represents a fluorine atom or a chlorine atom;

(9) the compound according to any one of (4) to (8), or a pharmacologically acceptable salt thereof, wherein Y represents a methoxy group, an ethoxy group or a propoxy group;

(10) the compound according to (2) represented by the following general formula (I-2) or a pharmacologically acceptable salt thereof:

[Formula 6]

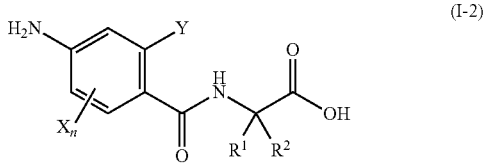

wherein $R^1$ represents an ethyl group; $R^2$ represents a $C_1$-$C_4$ alkyl group or a $C_3$-$C_4$ cycloalkyl group; n represents 0, 1 or 2; each X is the same or different, and represents a $C_1$-$C_4$ alkyl group, a $C_3$-$C_4$ cycloalkyl group, a halogen atom, a cyano group or a halogeno $C_1$-$C_4$ alkyl group; and Y represents a hydrogen atom, provided that X does not represent a halogen atom or a $C_1$-$C_4$ alkoxy group when $R^2$ represents an ethyl group, and neither X represents a $C_1$-$C_4$ alkoxy group when n represents 2;

(11) the compound according to (10) represented by the following general formula (I-2a) or a pharmacologically acceptable salt thereof:

[Formula 7]

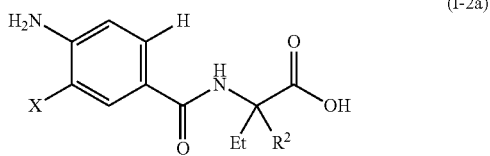

wherein $R^2$ represents a $C_1$-$C_3$ alkyl group or a cyclopropyl group; X represents a $C_1$-$C_3$ alkyl group, a fluorine atom, a chlorine atom or a bromine atom, provided that X does not represent a fluorine atom, a chlorine atom or a bromine atom when $R^2$ represents an ethyl group;

(12) the compound according to (11), or a pharmacologically acceptable salt thereof, wherein $R^2$ represents a methyl group, an ethyl group or a cyclopropyl group;

(13) the compound according to (11) or (12), or a pharmacologically acceptable salt thereof, wherein X represents a methyl group or a chlorine atom;

(14) the compound according to (2), selected from the group consisting of 2-[(4-amino-5-chloro-2-methoxybenzoyl)amino]-2-ethylbutanoic acid, (−)-N-(4-amino-5-fluoro-2-propoxybenzoyl)-D-isovaline, (+)-N-(4-amino-2-ethoxy-5-fluorobenzoyl)-L-isovaline, (−)-N-(4-amino-2-ethoxy-5-fluorobenzoyl)-D-isovaline, (+)-N-(4-amino-5-chloro-2-methoxybenzoyl)-L-isovaline, (−)-N-(4-amino-5-chloro-2-methoxybenzoyl)-D-isovaline, (+)-N-(4-amino-5-chloro-2-ethoxybenzoyl)-L-isovaline, (−)-N-(4-amino-5-chloro-2-ethoxybenzoyl)-D-isovaline, (−)-N-(4-amino-5-chloro-2-propoxybenzoyl)-D-isovaline, (+)-N-(4-amino-5-bromo-2-methoxybenzoyl)-L-isovaline, (−)-N-(4-amino-5-bromo-2-methoxybenzoyl)-D-isovaline, (+)-N-(4-amino-5-bromo-2-ethoxybenzoyl)-L-isovaline, (−)-N-(4-amino-5-bromo-2-ethoxybenzoyl)-D-isovaline, (+)-N-(4-amino-5-iodo-2-methoxybenzoyl)-L-isovaline, (−)-N-(4-amino-5-iodo-2-methoxybenzoyl)-D-isovaline, (+)-N-(4-amino-2-ethoxy-5-iodobenzoyl)-L-isovaline, and (−)-N-(4-amino-2-ethoxy-5-iodobenzoyl)-D-isovaline; or a pharmacologically acceptable salt thereof;

(15) a pharmaceutical composition comprising, as an active ingredient, the compound according to any one of (2) to (14) or a pharmacologically acceptable salt thereof;

(16) a crystalline form of the compound according to (2), selected from the group consisting of:
crystalline 2-[(4-amino-5-chloro-2-methoxybenzoyl)amino]-2-ethylbutanoic acid having characteristic peaks at interplanar spacings d of 7.51, 7.33, 6.67, 6.15, 5.32, 5.24, 4.98, 4.79, 3.96 and 3.59 angstroms;
crystalline (−)-N-(4-amino-5-fluoro-2-propoxybenzoyl)-D-isovaline having characteristic peaks at interplanar spacings d of 10.02, 7.39, 5.47, 5.00, 4.79, 4.70, 4.54, 4.39, 4.28 and 2.95 angstroms;
crystalline (−)-N-(4-amino-5-chloro-2-methoxybenzoyl)-D-isovaline having characteristic peaks at interplanar spacings d of 6.61, 5.96, 5.16, 5.10, 4.85, 4.68, 4.50, 4.08, 3.43 and 2.69 angstroms;
crystalline (−)-N-(4-amino-5-chloro-2-ethoxybenzoyl)-D-isovaline having characteristic peaks at interplanar spacings d of 10.67, 10.06, 5.33, 5.09, 5.02, 4.26, 4.14, 3.67, 3.47 and 2.96 angstroms;
crystalline (−)-N-(4-amino-5-chloro-2-propoxybenzoyl)-D-isovaline having characteristic peaks at interplanar spacings d of 8.89, 8.39, 6.07, 5.63, 5.15, 5.01, 4.22, 3.59, 3.39 and 2.76 angstroms;
crystalline (−)-N-(4-amino-5-bromo-2-methoxybenzoyl)-D-isovaline having characteristic peaks at interplanar spacings d of 10.37, 9.40, 6.12, 5.17, 4.87, 4.20, 3.89, 3.45, 3.05 and 2.84 angstroms;
crystalline (−)-N-(4-amino-5-bromo-2-ethoxybenzoyl)-D-isovaline having characteristic peaks at interplanar spacings d of 10.23, 6.38, 5.09, 5.04, 4.17, 4.11, 3.49 and 3.38 angstroms;
crystalline (−)-N-(4-amino-5-iodo-2-methoxybenzoyl)-D-isovaline having characteristic peaks at interplanar spacings d of 12.00, 5.99, 5.53, 5.17, 5.08, 3.68, 3.35, 3.06, 2.86 and 2.39 angstroms;
crystalline (+)-N-(4-amino-2-ethoxy-5-fluorobenzozyl)-L-isovaline having characteristic peaks at interplanar spacings d of 10.13, 6.35, 5.87, 5.08, 4.76, 4.16, 4.09, 3.60, 3.48 and 3.37 angstroms; and crystalline (−)-N-(4-amino-2-ethoxy-5-fluorobenzoyl)-D-isovaline having characteristic peaks at interplanar spacings d of 10.23, 6.38, 5.09, 5.04, 4.17, 4.11, 3.49 and 3.38 angstroms;
all in powder X-ray diffraction obtained through irradiation with copper Kα radiation (wavelength λ=1.54 angstroms);

(17) a pharmaceutical composition comprising, as an active ingredient, any one of the crystalline forms of the compound according to (16);

(18) the pharmaceutical composition according to (1), (15) or (17), wherein the pharmaceutical composition is a tryptophanase inhibitor;

(19) the pharmaceutical composition according to (1), (15) or (17), wherein the pharmaceutical composition is a pharmaceutical composition for reducing indoxyl sulfate in the blood;

(20) the pharmaceutical composition according to (1), (15) or (17), wherein the pharmaceutical composition is a pharmaceutical composition for suppressing worsening of renal function;

(21) the pharmaceutical composition according to (1), (15) or (17), for preventing or treating a disease caused by an increase in indoxyl sulfate in the blood;

(22) the pharmaceutical composition according to (1), (15) or (17), wherein the pharmaceutical composition is a pharmaceutical composition for delaying transition to renal replacement therapy in a patient in a period of conservative treatment of chronic kidney disease;

(23) the pharmaceutical composition according to (1), (15) or (17), wherein the pharmaceutical composition is a pharmaceutical composition for suppressing worsening of remaining renal function in a patient after transition to renal replacement therapy;

(24) an agent for reducing indoxyl sulfate in the blood, comprising, as an active ingredient, the compound according to any one of (2) to (14) or a pharmacologically acceptable salt thereof, or a crystalline form of the compound according to (16);

(25) an agent for preventing or treating a disease caused by an increase in indoxyl sulfate in the blood, comprising, as an active ingredient, the compound according to any one of (2) to (14) or a pharmacologically acceptable salt thereof, or a crystalline form of the compound according to (16);

(26) an agent for delaying transition to renal replacement therapy in a patient in a period of conservative treatment of chronic kidney disease, comprising, as an active ingredient, the compound according to any one of (2) to (14) or a pharmacologically acceptable salt thereof, or a crystalline form of the compound according to (16);

(27) an agent for suppressing worsening of remaining renal function in a patient after transition to renal replacement therapy, comprising, as an active ingredient, the compound according to any one of (2) to (14) or a pharmacologically acceptable salt thereof, or a crystalline form of the compound according to (16);

(28) use of the compound according to any one of (2) to (14) or a pharmacologically acceptable salt thereof, or a crystalline form of the compound according to (16), for producing a pharmaceutical composition;

(29) the use according to (28), for producing a pharmaceutical composition for preventing or treating a disease caused by an increase in indoxyl sulfate in the blood;

(30) the use according to (28), for producing a pharmaceutical composition for delaying transition to renal replacement therapy in a patient in a period of conservative treatment of chronic kidney disease;

(31) the use according to (28), for producing a pharmaceutical composition for suppressing worsening of remaining renal function in a patient after transition to renal replacement therapy;

(32) a method for reducing indoxyl sulfate in the blood, comprising administering, to a mammal, an effective dose of the compound according to any one of (2) to (14) or a pharmacologically acceptable salt thereof, or a crystalline form of the compound according to (16);

(33) the method according to (32), wherein the mammal is a human;

(34) a method for preventing or treating a disease, comprising administering, to a mammal, an effective dose of the compound according to any one of (2) to (14) or a pharmacologically acceptable salt thereof, or a crystalline form of the compound according to (16);

(35) the method according to (34), wherein the mammal is a human;

(36) the method according to (34) or (35), wherein the disease is a disease caused by an increase in indoxyl sulfate in the blood;

(37) the compound according to any one of (2) to (14) or a pharmacologically acceptable salt thereof, or a crystalline form of the compound according to (16), for use in a method for preventing or treating a disease; and

(38) the compound according to (37) or a pharmacologically acceptable salt thereof, wherein the disease is a disease caused by an increase in indoxyl sulfate in the blood.

Now, definitions of the substituents used in the inventive compound (I) will be described.

In the inventive compound (I), a "$C_1$-$C_6$ alkyl group" is a straight or branched saturated hydrocarbon group having 1 to 6 carbon atoms, and is, for example, a methyl group, an ethyl group, a propyl group, an isopropyl group, a butyl group, a sec-butyl group, a tert-butyl group, an isobutyl group, a pentyl group or a hexyl group, is preferably a straight or branched saturated hydrocarbon group having 1 to 4 carbon atoms ($C_1$-$C_4$ alkyl group), is more preferably a straight or branched saturated hydrocarbon group having 1 to 3 carbon atoms ($C_1$-$C_3$ alkyl group), is further preferably a methyl group, an ethyl group or a propyl group, and is particularly preferably a methyl group or an ethyl group.

In the inventive compound (I), a "halogen atom" is a fluorine atom, a chlorine atom, a bromine atom or an iodine atom, is preferably a fluorine atom, a chlorine atom or a bromine atom, and is more preferably a fluorine atom or a chlorine atom.

In the inventive compound (I), a "halogeno $C_1$-$C_6$ alkyl group" is the "$C_1$-$C_6$ alkyl group" substituted with the same or different one to three "halogen atoms" described above, and is, for example, a monofluoromethyl group, a monochloromethyl group, a difluoromethyl group, a dichloromethyl group, a chlorofluoromethyl group, a trifluoromethyl group or a 2,2,2-trifluoroethyl group, is preferably a methyl group or an ethyl group substituted with one to three fluorine atoms, is more preferably a difluoromethyl group, a trifluoromethyl group or a 2,2,2-trifluoroethyl group, and is particularly preferably a trifluoromethyl group.

In the inventive compound (I), a "$C_3$-$C_6$ cycloalkyl group" is a cyclic saturated hydrocarbon group having 3 to 6 carbon atoms, such as a cyclopropyl group, a cyclobutyl group, a cyclopentyl group or a cyclohexyl group, and is preferably a cyclic saturated hydrocarbon group having 3 to 4 carbon atoms, and is further preferably a cyclopropyl group.

In the inventive compound (I), a "$C_1$-$C_6$ alkoxy group" is an oxygen atom to which the "$C_1$-$C_6$ alkyl group" is bonded, and is, for example, a methoxy group, an ethoxy group, a propoxy group, an isopropoxy group or a butoxy group, is preferably an oxygen atom to which the "$C_1$-$C_4$ alkyl group" is bonded ($C_1$-$C_4$ alkoxy group), is more preferably an oxygen atom to which the "$C_1$-$C_3$ alkyl group" is bonded ($C_1$-$C_3$ alkoxy group), and is further preferably a methoxy group or an ethoxy group.

In the inventive compound (I), a "halogeno $C_1$-$C_6$ alkoxy group" is an oxygen atom to which the "halogeno $C_1$-$C_6$ alkyl group" is bonded, and is, for example, a monofluoromethoxy group, a difluoromethoxy group or a trifluoromethoxy group, and is preferably a difluoromethoxy group or a trifluoromethoxy group.

In the inventive compound (I), a "$C_3$-$C_6$ cycloalkoxy group" is an oxygen atom to which the "$C_3$-$C_6$ cycloalkyl group" is bonded, and is, for example, a cyclopropyloxy group, a cyclobutyloxy group, a cyclopentyloxy group or a cyclohexyloxy group, and is preferably a cyclopropyloxy group.

Specific examples of preferable compounds of the inventive compound (I) include: 2-[(4-amino-5-chloro-2-methoxybenzoyl)amino]-2-ethylbutanoic acid, (−)-N-(4-amino-5-fluoro-2-propoxybenzoyl)-D-isovaline, (+)-N-(4-amino-5-chloro-2-methoxybenzoyl)-L-isovaline, (−)-N-(4-amino-5-chloro-2-methoxybenzoyl)-D-isovaline, (+)-N-(4-amino-5-chloro-2-ethoxybenzoyl)-L-isovaline, (−)-N-(4-amino-5-chloro-2-ethoxybenzoyl)-D-isovaline, (−)-N-(4-amino-5-chloro-2-propoxybenzoyl)-D-isovaline, (+)-N-(4- amino-5-bromo-2-methoxybenzoyl)-L-isovaline, (−)-N-(4-amino-5-bromo-2-methoxybenzoyl)-D-isovaline, (+)-N-(4-amino-5-bromo-2-ethoxybenzoyl)-L-isovaline, (−)-N-(4-amino-5-bromo-2-ethoxybenzoyl)-D-isovaline, (+)-N-(4-amino-5-iodo-2-methoxybenzoyl)-L-isovaline, (−)-N-(4-amino-5-iodo-2-methoxybenzoyl)-D-isovaline, (+)-N-(4-amino-2-ethoxy-5-fluorobenzoyl)-L-isovaline, (−)-N-(4-amino-2-ethoxy-5-fluorobenzoyl)-D-isovaline, (+)-N-(4-amino-2-ethoxy-5-iodobenzoyl)-L-isovaline, and (−)-N-(4-amino-2-ethoxy-5-iodobenzoyl)-D-isovaline.

In the inventive compound (I), the term "a pharmacologically acceptable salt thereof" refers to a salt usable as a pharmaceutical. When a compound has an acidic group or a basic group, the compound can be changed into a "salt with a base" or an "acid addition salt" through reaction with a base or an acid, and the term refers to such a salt.

Preferable examples of the pharmacologically acceptable "salt with a base" of the compound include alkali metal salts such as sodium salts, potassium salts and lithium salts; alkaline earth metal salts such as magnesium salts and calcium salts; organic basic salts such as N-methylmorpholine salts, triethylamine salts, tributylamine salts, diisopropylethylamine salts, dicyclohexylamine salts, N-methylpiperidine salts, pyridine salts, 4-pyrrolidinopyridine salts and picoline salts, or amino acid salts such as glycine salts, lysine salts, arginine salts, ornithine salts, glutamic acid salts and aspartic acid salts, and alkali metal salts or alkaline earth metal salts are preferable.

Preferable examples of the pharmacologically acceptable "acid addition salt" of the compound include inorganic acid salts such as hydrohalogenic acid salts like hydrofluoric acid salts, hydrochloric acid salts, hydrobromic acid salts and hydroiodic acid salts, nitric acid salts, perchloric acid salts, sulfuric acid salts and phosphoric acid salts; organic acid salts such as lower alkanesulfonic acid salts like methanesulfonic acid salts, trifluoromethanesulfonic acid salts and ethanesulfonic acid salts, arylsulfonic acid salts like benzenesulfonic acid salts and p-toluenesulfonic acid salts, acetic acid salts, malic acid salts, fumaric acid salts, succinic acid salts, citric acid salts, ascorbic acid salts, tartaric acid salts, oxalic acid salts and maleic acid salts; and amino acid salts such as glycine salts, lysine salts, arginine salts, ornithine salts, glutamic acid salts and aspartic acid salts, and hydrohalogenic acid salts (particularly hydrochloric acid salts) are most preferable.

The inventive compound (I) or a pharmacologically acceptable salt thereof may absorb moisture when left in air to be changed into a hydrate, and such a hydrate is also embraced in the present invention.

The inventive compound (I) or a pharmacologically acceptable salt thereof may be changed into a solvate when left in a solvent, and such a solvate is also embraced in the present invention.

The inventive compound (I) or a pharmacologically acceptable salt thereof includes crystalline forms thereof. The crystalline forms of the present invention refer to solids having an internal structure three-dimensionally composed of regularly repeated constituent atoms (or a group thereof), and are distinguished from amorphous solids not having such a regular internal structure.

Even crystals of the same compound may be produced in the form of a plurality of crystalline forms (crystal polymorphs) having different internal structures and physiochemical properties depending on crystallization conditions, and the crystalline form of the present invention may be any one of the crystal polymorphs, or may be a mixture of two or more crystal polymorphs.

The crystalline forms of the present invention may form hydrates by absorbing moisture to have water attached thereto when left in air or by heating to 25 to 150° C. under usual atmospheric conditions. Besides, the crystalline forms of the present invention may contain, as attached residual solvent or a solvate, a solvent used at the time of the crystallization.

In the present description, the crystalline forms of the present invention may sometimes be expressed based on powder X-ray diffraction data. For powder X-ray diffraction, the measurement/diffraction may be performed under conditions usually employed in the field of the present invention, and can be performed, for example, by a method described in an example. Besides, in general, a hydrate or a dehydrated form is changed in its lattice constant through attachment/detachment of water of crystallization, which may change a diffraction angle (2θ) in the powder X-ray diffraction. Furthermore, peak intensity may be changed by a difference (crystal habit) of a growth surface of the crystal in some cases. Accordingly, when the crystalline forms of the present invention are expressed based on powder X-ray diffraction data, not only crystals having the same diffraction angle at a peak and X-ray diffraction diagram in the powder X-ray diffraction, but also hydrates and dehydrated forms obtained from the crystals, are embraced in the scope of the present invention.

Specific examples of the crystalline forms of the inventive compound (I) include crystalline 2-[(4-amino-5-chloro-2-methoxybenzoyl)amino]-2-ethylbutanoic acid having, in powder X-ray diffraction obtained through irradiation with copper Kα radiation (wavelength 1=1.54 angstroms), characteristic peaks at interplanar spacings d of 7.51, 7.33, 6.67, 6.15, 5.32, 5.24, 4.98, 4.79, 3.96 and 3.59 angstroms. This crystalline form presents the powder X-ray diffraction diagram of FIG. 1 through irradiation with copper Kα radiation (wavelength λ=1.54 angstroms).

In each of the powder X-ray diffraction patterns illustrated in FIG. 1 and FIGS. 2 to 10 mentioned below, the ordinate indicates diffraction intensity in count/sec. (CPS), and the abscissa indicates diffraction angle 2θ (degrees). Besides, the interplanar spacing d (unit: angstrom) can be calculated in accordance with an expression, $2d \sin \theta = n\lambda$ with n set to 1.

Another preferable specific example of the present invention includes crystalline (−)-N-(4-amino-5-fluoro-2-propoxybenzoyl)-D-isovaline having, in powder X-ray diffraction obtained through irradiation with copper Ku radiation (wavelength λ=1.54 angstroms), characteristic peaks at interplanar spacings d of 10.02, 7.39, 5.47, 5.00, 4.79, 4.70, 4.54, 4.39, 4.28 and 2.95 angstroms. This crystalline form presents the powder X-ray diffraction diagram of FIG. 2 through irradiation with copper Kα radiation (wavelength λ=1.54 angstroms).

Still another preferable specific example of the present invention includes crystalline (−)-N-(4-amino-5-chloro-2-methoxybenzoyl)-D-isovaline having, in powder X-ray diffraction obtained through irradiation with copper Kα radiation (wavelength λ=1.54 angstroms), characteristic peaks at interplanar spacings d of 6.61, 5.96, 5.16, 5.10, 4.85, 4.68, 4.50, 4.08, 3.43 and 2.69 angstroms. This crystalline form presents the powder X-ray diffraction diagram of FIG. 3 through irradiation with copper Kα radiation (wavelength λ=1.54 angstroms).

Still another preferable specific example of the present invention includes crystalline (−)-N-(4-amino-5-chloro-2-ethoxybenzoyl)-D-isovaline having, in powder X-ray dif-fraction obtained through irradiation with copper Kα radiation (wavelength λ=1.54 angstroms), characteristic peaks at interplanar spacings d of 10.67, 10.06, 5.33, 5.09, 5.02, 4.26, 4.14, 3.67, 3.47 and 2.96 angstroms. This crystalline form presents the powder X-ray diffraction diagram of FIG. 4 through irradiation with copper Kα radiation (wavelength λ=1.54 angstroms).

Still another preferable specific example of the present invention includes crystalline (−)-N-(4-amino-5-chloro-2-propoxybenzoyl)-D-isovaline having, in powder X-ray diffraction obtained through irradiation with copper Kα radiation (wavelength λ=1.54 angstroms), characteristic peaks at interplanar spacings d of 8.89, 8.39, 6.07, 5.63, 5.15, 5.01, 4.22, 3.59, 3.39 and 2.76 angstroms. This crystalline form presents the powder X-ray diffraction diagram of FIG. 5 through irradiation with copper Kα radiation (wavelength λ=1.54 angstroms).

Still another preferable specific example of the present invention includes crystalline (−)-N-(4-amino-5-bromo-2-methoxybenzoyl)-D-isovaline having, in powder X-ray diffraction obtained through irradiation with copper Kα radiation (wavelength λ=1.54 angstroms), characteristic peaks at interplanar spacings d of 10.37, 9.40, 6.12, 5.17, 4.87, 4.20, 3.89, 3.45, 3.05 and 2.84 angstroms. This crystalline form presents the powder X-ray diffraction diagram of FIG. 6 through irradiation with copper Kα radiation (wavelength λ=1.54 angstroms).

Still another preferable specific example of the present invention includes crystalline (−)-N-(4-amino-5-bromo-2-ethoxybenzoyl)-D-isovaline having, in powder X-ray diffraction obtained through irradiation with copper Kα radiation (wavelength λ=1.54 angstroms), characteristic peaks at interplanar spacings d of 10.23, 6.38, 5.09, 5.04, 4.17, 4.11, 3.49 and 3.38 angstroms. This crystalline form presents the powder X-ray diffraction diagram of FIG. 7 through irradiation with copper Kα radiation (wavelength λ=1.54 angstroms).

Still another preferable specific example of the present invention includes crystalline (−)-N-(4-amino-5-iodo-2-methoxybenzoyl)-D-isovaline having, in powder X-ray diffraction obtained through irradiation with copper Kα radiation (wavelength λ=1.54 angstroms), characteristic peaks at interplanar spacings d of 12.00, 5.99, 5.53, 5.17, 5.08, 3.68, 3.35, 3.06, 2.86 and 2.39 angstroms. This crystalline form presents the powder X-ray diffraction diagram of FIG. 8 through irradiation with copper Kα radiation (wavelength λ=1.54 angstroms).

Still another preferable specific example of the present invention includes crystalline (+)-N-(4-amino-2-ethoxy-5-fluorobenzoyl)-L-isovaline having, in powder X-ray diffraction obtained through irradiation with copper Kα radiation (wavelength λ=1.54 angstroms), characteristic peaks at interplanar spacings d of 10.13, 6.35, 5.87, 5.08, 4.76, 4.16, 4.09, 3.60, 3.48 and 3.37 angstroms. This crystalline form presents the powder X-ray diffraction diagram of FIG. 9 through irradiation with copper Kα radiation (wavelength λ=1.54 angstroms).

Still another preferable specific example of the present invention includes crystalline (−)-N-(4-amino-2-ethoxy-5-fluorobenzoyl)-D-isovaline having, in powder X-ray diffraction obtained through irradiation with copper Kα radiation (wavelength λ=1.54 angstroms), characteristic peaks at interplanar spacings d of 10.23, 6.38, 5.09, 5.04, 4.17, 4.11, 3.49 and 3.38 angstroms. This crystalline form presents the powder X-ray diffraction diagram of FIG. 10 through irradiation with copper Kα radiation (wavelength λ=1.54 angstroms).

Since the inventive compound (I) has a carboxyl group, a compound obtained by converting the carboxyl group into a pharmacologically acceptable prodrug is also embraced in the present invention. The term "a pharmacologically acceptable prodrug" refers to a compound that is converted into the inventive compound (I) through a reaction with an enzyme, a gastric acid or the like under physiological conditions in a living body, namely, a compound changed into the inventive compound (I) through enzymatically caused oxidation, reduction, hydrolysis or the like, or a compound changed into the inventive compound (I) through hydrolysis or the like caused by gastric acid or the like.

Examples of such a prodrug include compounds obtained through esterification, amidation or the like of the carboxyl group of the inventive compound (I) (for example, compounds obtained through ethyl esterification, phenyl esterification, carboxymethyl esterification, dimethylaminomethyl esterification, pivaloyloxymethyl esterification, ethoxycarbonyloxy ethyl esterification, phthalidyl esterification, (5-methyl-2-oxo-1,3-dioxolen-4-yl)methyl esterification, cyclohexyloxy carbonylethyl esterification, sulfate esterification, glucuronidation, glycosidation, galactosidation and methyl amidation of the carboxyl group).

A pharmacologically acceptable prodrug of the inventive compound (I) can be easily produced from the compound (I) of the present invention by a known method. Besides, a prodrug of the compound of the present invention includes those changed into the inventive compound (I) under physiological conditions described in "Iyakuhin no Kaihatsu (Development of Pharmaceuticals)", vol. 7 Bunshi Sekkei (Molecular Design), pp. 163-198, published by Hirokawa Shoten Co. in 1990.

The inventive compound (I) may produce a geometric isomer or a tautomer depending on the selected substituents, and an isolated compound of such isomers and mixtures thereof in an arbitrary ratio are embraced in the present invention.

The inventive compound (I) may have optical isomers based on asymmetric center(s) in the molecule. Unless otherwise specified, in the compound of the present invention, such isomer and mixtures of such isomers are all represented by a single formula, namely, general formula (I). Accordingly, it is noted that the present invention embraces all of these isomers and mixtures of these isomers.

In the inventive compound (I), for example, when either one of R or $R^2$ is a methyl group and the other is a $C_2$-$C_6$ alkyl group, both the (R) form and the (S) form are preferable as optical isomers based on the asymmetric center to which $R^1$ and $R^2$ bind, and the (R) form is more preferable.

A mixture of these isomers can be separated by known separation means.

The inventive compound (I) can contain an atomic isotope of one or more atoms constituting the compound at a non-natural ratio. Examples of the atomic isotope include deuterium ($^2H$), tritium ($^3H$), iodine-125 ($^{125}I$) and carbon-14 ($^{14}C$). Besides, the compound can be radiolabeled with a radioisotope such as tritium ($^3H$), iodine-125 ($^{125}I$) or carbon-14 ($^{14}C$). The thus radiolabeled compound is useful as a therapeutic or prophylactic agent, a research reagent such as an assay reagent, and a diagnostic agent such as an in vivo image diagnostic agent. It is noted that all isotopic variants of the compound of the present invention are embraced in the scope of the present invention no matter whether or not they are radioactive.

Advantageous Effects of Invention

The inventive compound (I) or a pharmacologically acceptable salt thereof has excellent tryptophanase inhibitory function and is useful as an agent for reducing indoxyl sulfate in the blood, an agent for preventing or treating a disease caused by an increase in indoxyl sulfate in the blood, an agent for delaying transition to renal replacement therapy in a patient in a period of conservative treatment of chronic kidney disease, and an agent for suppressing worsening of remaining renal function in a patient after transition to renal replacement therapy.

DESCRIPTION OF EMBODIMENTS

Figure 1:
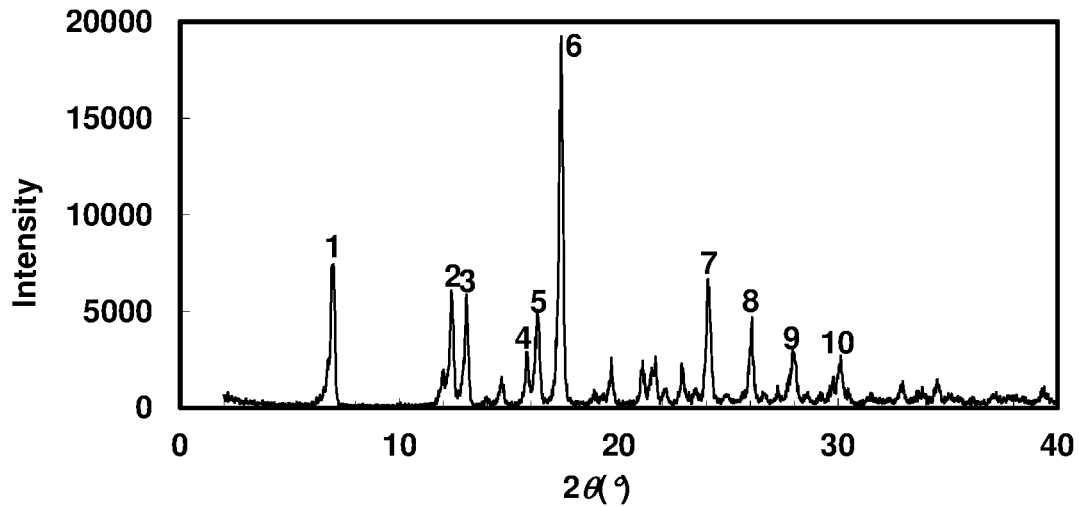
FIG. 1 is a powder X-ray diffraction diagram of crystals obtained in Example 6. The ordinate indicates diffraction intensity in count/sec. (cps), and the abscissa indicates a value of diffraction angle 2θ.

The compound of the present invention and pharmacologically acceptable salts thereof can be produced by applying a variety of known synthesis methods based on the characteristics of the basic structure or the type of substituent(s) of the compound to be produced.

In the production, depending on the type of a functional group, it may be effective in terms of production technology, in some cases, to replace the functional group with an appropriate protective group (a group that can be easily converted into the functional group) at a stage from raw material to intermediate. Examples of such protective groups include protective groups described in Greene's Protective Groups in Organic Synthesis, written by P. G. M. Wuts and T. W. Greene (4th edition, 2006), and the protective group may be appropriately selected in accordance with reaction conditions for these.

In such a method, a reaction is performed by introducing the protective group, and then, the protective group is removed if necessary, and thus a desired compound can be obtained. Besides, a prodrug of the compound of the present invention can be produced, at a stage from raw material to intermediate similarly to the protective group, by introducing a specific group or by further performing a reaction using a resultant compound. The reaction can be performed by applying a usual method of esterification, amidation, dehydration or the like.

Now, representative methods for producing the inventive compound (I) and starting compounds used in the production of the compound (I) of the present invention will be described, and it is noted that the present invention is not limited to these methods.

[Method A]

Method A is a method for producing the inventive compound (I).

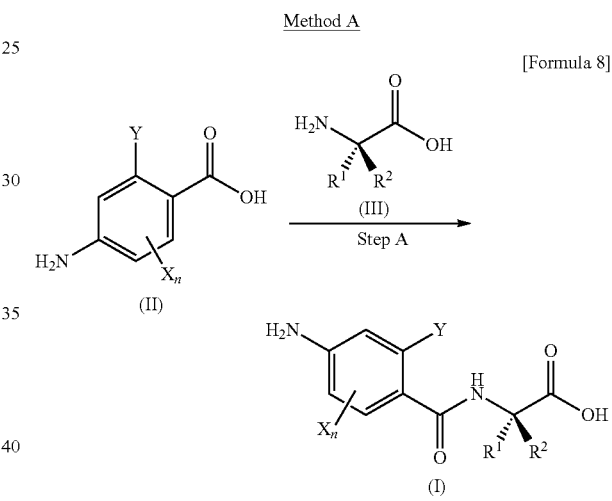

In the formula, X, n, Y, $R^1$ and $R^2$ are as defined above.

(Step A) Step of Forming Amide by Condensation

This step is a step of producing the compound (I) by reacting a compound (II) and a compound (III) with a condensing agent in the presence or absence of a base.

The reaction temperature in this step is usually room temperature to 80° C., and the reaction time in this step is usually 1 hour to 24 hours.

As a base used in this step, a tertiary amine such as triethylamine, N,N-diisopropylethylamine or N-methylmorpholine is preferable.

Examples of the condensing agent used in this step include O-(benzotriazol-1-yl)-N,N,N',N'-tetramethyluronium hexafluorophosphate, O-(7-azabenzotriazol-1-yl)-N,N,N',N'-tetramethyluronium hexafluorophosphate and (1-cyano-2-ethoxy-2-oxoethylideneaminooxy)dimethylamino-morpholino-carbenium hexafluorophosphate.

As a solvent used in this step, for example, N,N-dimethylformamide or N,N-dimethylacetamide is preferable.

The compound (II) can be obtained as a commercially available product, or can be produced by a known method or an equivalent method, or a method described later.

Besides, the compound (III) can be obtained as a commercially available product, or can be produced by a known method (for example, Tetrahedron: Asymmetry, 2007, 18, 569-623) or an equivalent method.

[Method B]

Method B is a method for producing the compound (II) used in the method A.

Method B

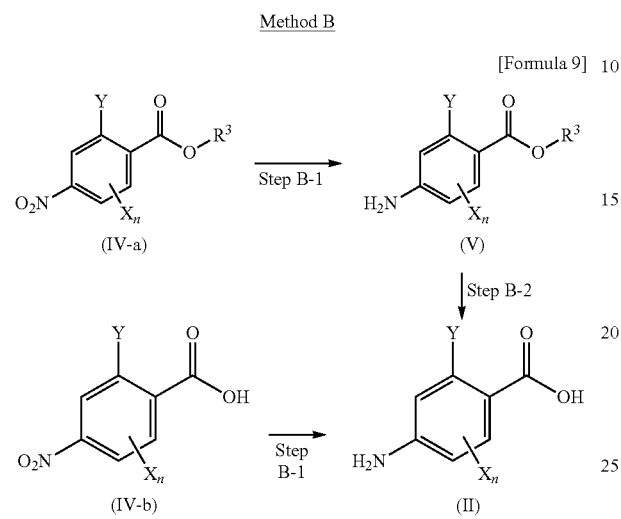

[Formula 9]

(IV-a) → (V)
(IV-b) → (II)

In the formula, X, n and Y are as defined above, and $R^3$ represents a $C_1$-$C_6$ alkyl group such as a methyl group, an ethyl group or a propyl group.

(Step B-1) Step of Reducing a Nitro Group to an Amino Group

This step is a step of obtaining a compound (V) by reducing a solution of a compound (IV-a) under a hydrogen atmosphere in the presence of a metal catalyst such as 10% palladium carbon.

The solvent used in this step is preferably an alcohol such as methanol, ethanol or the like.

The reaction temperature in this step is usually room temperature, and the reaction time in this step is usually 1 hour to 12 hours.

(Step B-2) Step of Hydrolyzing Ester

This step is a step of obtaining the compound (II) by hydrolyzing an ester group of the compound (V) in a solvent in the presence of a base.

The base used in this step is preferably an alkali metal hydroxide such as sodium hydroxide or potassium hydroxide, and the solvent used in this step is, for example, preferably a mixed solvent of water and tetrahydrofuran/methanol.

The reaction temperature in this step is usually room temperature to 80° C., and the reaction time in this step is usually 1 hour to 24 hours.

The compound (IV) can be obtained as a commercially available product, or can be produced by a known method or an equivalent method or by protecting a carboxylic acid moiety of the compound (IV-b) (for example, Greene's Protective Groups in Organic Synthesis, written by P. G. M. Wuts and T. W. Greene (4th edition, 2006)).

[Method C]

Method C is a method for producing the compound (II) used in the method A, and is an alternative method to the method B.

Method C

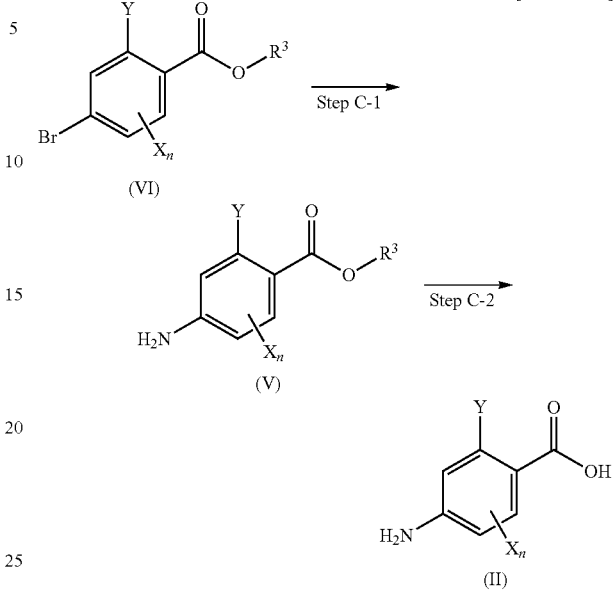

[Formula 10]

(VI) → (V) → (II)

In the formula, X, n, Y and $R^3$ are as defined above.

(Step C-1) Step of Introducing an Amino Group

This step is a step of producing a compound (V) by performing a reaction by adding benzophenonimine to a solution of a compound (VI) in the presence of a catalyst, a ligand and a base, followed by treating with an acid.

Examples of the catalyst used in this step include palladium acetate (II) and tris(dibenzylideneacetone)dipalladium (0), examples of the ligand include 4,5-bis(diphenylphosphino)-9,9-dimethylxanthene and 2,2'-bis(diphenylphosphino)-1,1'-binaphthalene, and examples of the base include cesium carbonate and sodium tert-butoxide.

As a solvent used in this step, for example, an ether such as 1,4-dioxane or toluene is preferred.

The reaction temperature in this step is usually 80 to 100° C., and the reaction time in this step is usually 1 hour to 24 hours.

Besides, the acid used in this step is usually hydrochloric acid, the reaction temperature in this step is usually room temperature, and the reaction time in this step is usually 1 to 12 hours.

(Step C-2) Step of Hydrolyzing Ester

This step is a step of producing the compound (II) under conditions similar to those of the step B-2 of the method B.

The compound (VI) can be obtained as a commercially available product, or can be produced by a known method or an equivalent method.

[Method D]

Method D is a method for producing a compound represented by the general formula (II-a) of the compounds (II) used in the method A, and is an alternative method to the method B and the method C. In the method B and the method C, a substituent corresponding to $X^1$ is already introduced in the first step but when the substituent corresponding to $X^1$ is a substituent corresponding to a halogen atom or a haloalkyl group, the compound can also be produced, as in the method D, via step D-1 and step D-2.

Method D

[Formula 11]

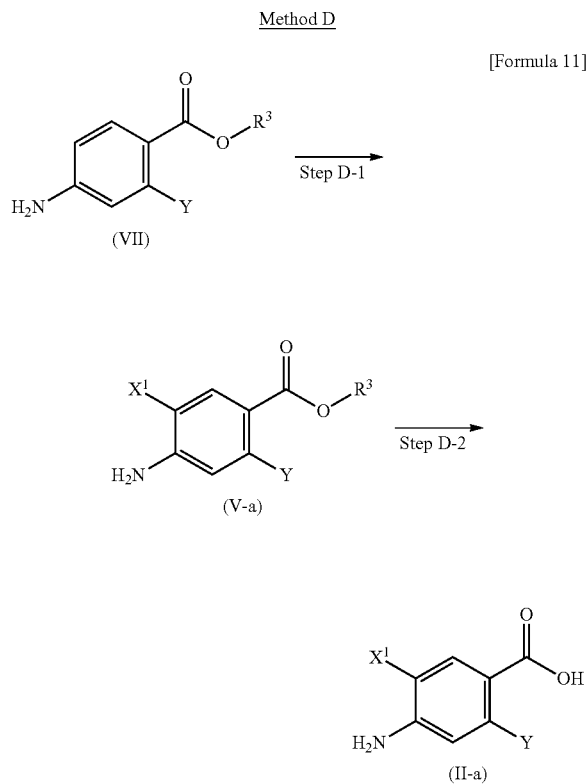

In the formula, Y and $R^3$ are as defined above, $X^1$ represents a halogen atom such as a chlorine atom, a bromine atom or an iodine atom, or a haloalkyl group such as a trifluoromethyl group.

(Step D-1) Step of Introducing a Substituent to a Position adjacent to an Amino Group This step is a step of introducing a halogen atom such as a chlorine atom, a bromine atom or an iodine atom, or a haloalkyl group such as a trifluoromethyl group, at a position adjacent to the amino group of a compound (VII).

In this step, the reaction is performed by adding, for example, N-bromosuccinimide, N-chlorosuccinimide, N-iodosuccinimide or 2-chloro-1,3-bis(methoxycarbonyl)guanidine (Palau' Chlor (registered trademark)), or the reaction is performed by adding (3,3-dimethyl-1-(trifluoromethyl)-1,2-benziodoxol or the like in the presence of chlorotris(trimethylsilyl)silane.

As a solvent used in this step, for example, a halogen such as dichloromethane, chloroform or carbon tetrachloride or acetonitrile or ethyl acetate is preferable.

The reaction temperature in this step is usually room temperature to 80° C.

(Step D-2) Step of Hydrolyzing Ester

This step is a step of producing a compound (II-a) under conditions similar to those of the step B-2 of the method B.

The compound (VII) can be obtained as a commercially available product or can be produced by a known method or an equivalent method, or a method described later.

[Method E]

Method E is a method for producing a compound (VII-a), wherein Y represents a $C_1$-$C_6$ alkoxy group, of the compound (VII) used in the method D.

Method E

[Formula 12]

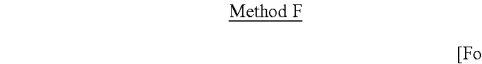

In the formula, $Y^a$ represents a $C_1$-$C_6$ alkoxy group, and $R^3$ is as defined above.

(Step E-1) Step of Alkylating a Phenolic Hydroxyl Group

This step is a step of producing a compound (IX) by adding a $C_1$-$C_6$ alkyl halide to a solution of a compound (VIII) in the presence of a base.

As a base used in this step, an inorganic base such as potassium carbonate or cesium carbonate is usually preferable.

Examples of the solvent used in this step include any of various solvents such as N,N-dimethylformamide, acetone and acetonitrile.

The reaction temperature in this step is usually room temperature to 80° C., and the reaction time in this step is usually 1 hour to 24 hours.

(Step E-2) Step of Reducing a Nitro Group to an Amino Group

This step is a step of producing the compound (VII-a) under conditions similar to those of the step B-1 of the method B.

The compound (VIII) can be obtained as a commercially available product, or can be produced by a known method or an equivalent method.

[Method F]

Method F is a method for producing a compound represented by the general formula (II-b) of the compounds (II) used in the method A, and is an alternative method to the method B, the method C and the method D. When a substituent corresponding to $X^2$ is a nitrile group, the compound can also be produced, as in the method F, via step F-1.

Method F

[Formula 13]

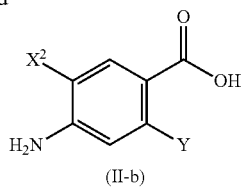

(II-b)

In the formula, Y is as defined above, and $X^2$ represents a nitrile group.

(Step F-1) Step of Performing Coupling using a Transition Metal Catalyst

This step is a step of producing a compound (II-b) by adding a potassium hexacyanoferrate(II) trihydrate or the like to a solution of a compound (V-b) in the presence of a catalyst, a ligand and a base.

Examples of the catalyst used in this step include [2-(di-tert-butylphosphino)-2',4',6'-triisopropyl-1,1'-biphenyl][2-(2-aminoethyl)phenyl]palladium(II) chloride, examples of the ligand used in this step include 2-di-tert-butylphosphino-2',4',6'-triisopropylbiphenyl, and examples of the base used in this step include potassium acetate.

Examples of the solvent used in this step include, other than ethers, any of various solvents such as N,N-dimethylformamide, toluene and acetonitrile.

The reaction temperature in this step is usually room temperature to 110° C., and the reaction time in this step is usually 1 hour to 24 hours.

The compound (V-b) can be obtained as a commercially available product or can be produced by a known method or an equivalent method, or the method D.

[Method G]

Method G is a method for producing the compound (I) of the present invention, and is an alternative method to the method A.

In the formula, X, n, Y, $R^1$ and $R^2$ are as defined above, and $R^4$ is a $C_1$-$C_6$ alkyl group such as a methyl group, an ethyl group or a propyl group.

(Step G-1) Step of Forming Amide by Condensation

This step is a step of producing the compound (IX) by reacting the compound (II) with a compound (X) wherein a carboxylic acid moiety is protected by a $C_1$-$C_6$ alkyl group and can be performed under conditions similar to those of the step A-1 of the method A.

(Step G-2) Step of Hydrolyzing Ester

This step is a step of producing the compound (I) under conditions similar to those of the step B-2 of the method B.

The compound (X) can be obtained as a commercially available product, or can be produced by a known method or an equivalent method or by protecting a carboxylic acid moiety of the compound (III) (for example, Greene's Protective Groups in Organic Synthesis, written by P. G. M. Wuts and T. W. Greene (4th edition, 2006)).

[Method H]

Method H

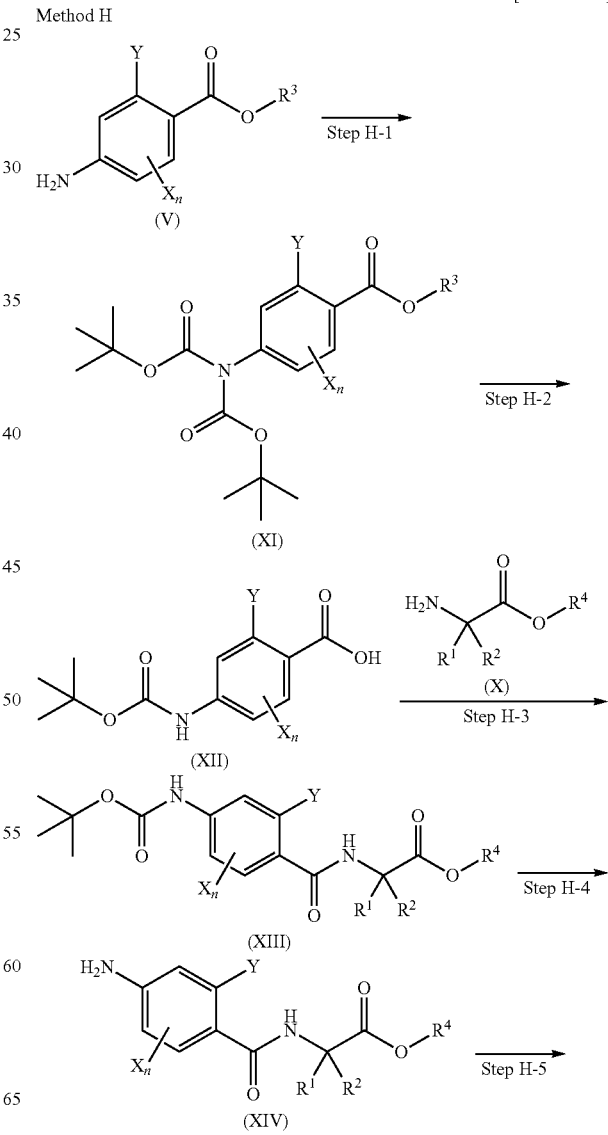

Method G

[Formula 14]

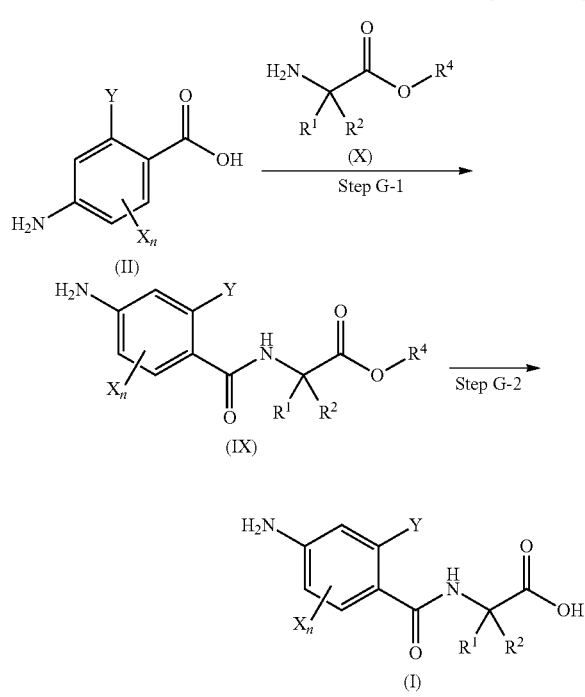

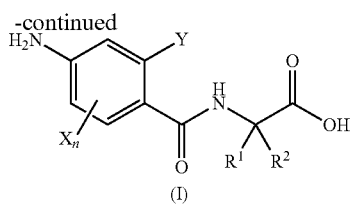

In the formula, X, n, Y, $R^1$, $R^2$, $R^3$ and $R^4$ are as defined above.

Method H is a method for producing the compound (I) of the present invention, and is an alternative method to the method A and the method G.

(Step H-1) Step of Protecting an Amino Group with a Tert-Butoxy Group

This step is a step of producing a compound (XI), usually by adding di-tert-butyl dicarbonate to a solution of the compound (V) in dichloromethane in the presence of 4-dimethylaminopyridine and triethylamine.

The reaction temperature in this step is usually room temperature, and the reaction time in this step is usually 1 hour to 24 hours.

(Step H-2) Step of Hydrolyzing

This step is a step of producing a compound (XII) under conditions similar to those of the step B-2 of the method B.

(Step H-3) Step of Forming Amide by Condensation

This step is a step of producing a compound (XIII) by reacting the compound (XII) wherein an amino group moiety is protected with the compound (X) wherein a carboxylic acid moiety is protected, and can be performed under conditions similar to those of the step A-1 of the method A.

(Step H-4) Step of Removing a Tert-Butoxy Group by an Acid

This step is a step of producing a compound (XIV), usually by performing a deprotection reaction by adding a 4N hydrochloric acid-ethyl acetate solution, trifluoroacetic acid, or the like to a solution of the compound (XIII).

The reaction temperature in this step is usually room temperature, and the reaction time in this step is usually 1 hour to 12 hours.

(Step H-5) Step of Hydrolyzing Ester

This step is a step of producing the compound (I) under conditions similar to those of the step B-2 of the method B.

The compound (II-b) can be obtained as a commercially available product, or can be produced by a known method or an equivalent method, or the method C, the method D or the method E.

A compound produced by the above-described method can be isolated and purified by a known method, such as extraction, precipitation, distillation, chromatography, fractional crystallization or recrystallization.

Besides, when the compound or a production intermediate has asymmetric carbon(s), it has optical isomers. Such optical isomers can be isolated and purified by a usual method such as fractional crystallization by recrystallizing with an appropriate salt (salt resolution) or column chromatography. For a method for resolving an optical isomer from a racemate, "Enantiomers, Racemates and Resolution, John Wiley and Sons, Inc." written by J. Jacques et al. can be referred to.

The inventive compound (I) or a pharmacologically acceptable salt thereof, or a crystalline form thereof, can reduce indoxyl sulfate in the blood. In the present invention, the term "reduce indoxyl sulfate in the blood" refers to reducing indoxyl sulfate concentration in human blood as compared with a value obtained before administering the inventive compound, and preferably reducing the indoxyl sulfate concentration in human blood as compared with a value obtained before administering the inventive compound by 0.1 mg/dL or more. For example, the indoxyl sulfate concentration in the blood of a kidney disease patient in CKD-stage 4, which is 0.45 md/dL on average, is reduced preferably to 0.24 mg/dL, that is, to the concentration of a kidney disease patient in CKD-stage 3; is reduced more preferably to 0.13 mg/dL, that is, to the concentration of a kidney disease patient in CKD-stage 2; and is reduced most preferably to 0.075 mg/dL, that is, to the level in a human not suffering from kidney disease. The indoxyl sulfate concentration in the blood of a terminal kidney disease patient including a dialysis patient in CKD-stage 5, which is 1.30 md/dL on average, is reduced preferably to 0.45 mg/dL, that is, to the concentration of a kidney disease patient in CKD-stage 4; is reduced more preferably to 0.24 mg/dL, that is, to the concentration of a kidney disease patient in CKD-stage 3; is reduced further more preferably to 0.13 mg/dL, that is, to the concentration of a kidney disease patient in CKD-stage 2; and is reduced most preferably to 0.075 mg/dL, that is, to the level in a human not suffering from kidney disease (ELLIS-RJ Nephrology 21 170-177 (2016)). The concentration of indoxyl sulfate in the blood can be quantitatively determined by singly employing liquid chromatography (fluorescence detection) or its combination with a mass spectrometer used successively.

The inventive compound (I) or a pharmacologically acceptable salt thereof, or a crystalline form thereof, can suppress worsening of renal function. In the present invention, the term "suppress worsening of renal function" refers to reducing leakage of protein such as albumin into urine, suppressing deterioration of GFR (glomerular filtration rate), or suppressing an increase in a biochemical marker in the blood and urine reflecting dysfunction of the kidney.

The inventive compound (I) or a pharmacologically acceptable salt thereof, or a crystalline form thereof, can prevent or treat a disease caused by an increase in indoxyl sulfate in the blood. In the present invention, the term "a disease caused by an increase in indoxyl sulfate in the blood" refers to chronic kidney disease (CKD), renal anemia, obstructive arteriosclerosis or ischemic heart disease, and is particularly chronic kidney disease.

In the present invention, the term "prevent" refers to reducing the probability of developing a disease caused by an increase in indoxyl sulfate in the blood. For example, when the disease caused by an increase in indoxyl sulfate in the blood is CKD, it refers to the probability of developing CKD in the future for a person with normal renal function having a soluble urokinase plasminogen activator receptor (suPAR) concentration in the blood of 4020 pg/mL or higher being reduced as compared with that of a person with normal renal function having a suPAR concentration in the blood lower than 2373 pg/mL (by three times or more, HR: 3.13: Hayek-S S, N Engl J Med 373: 1916-1925, 2015). The probability of developing CKD can be checked based on whether an estimated GFR<60 mL/min/1.73 $m^2$.

In the present invention, the term "treat" refers to suppressing advance or progression of pathological conditions of a disease caused by an increase in indoxyl sulfate in the blood, or improving the pathological conditions.

When the disease caused by an increase in indoxyl sulfate in the blood is CKD, the term "suppress advance or progression" refers to preventing an increase in leakage of protein such as albumin into urine, maintaining the GFR, and maintaining or suppressing an increase in a biochemical marker in the blood and urine reflecting the dysfunction of the kidney. It can be checked, for example, whether proteinuria of 0.3 g/gCr and albuminuria of 100 mg/gCr or more of a CKD patient is maintained for 6 months to 1 year, or by maintaining an eGFR of 30 mL/min/1.73 m$^2$ of a CKD patient for 6 months to 1 year. The term "improve pathological conditions" refers to lowering severity of CKD to a lower rank. For example, it can be checked whether albumin in urine of 0.6 g/gCr is reduced to 0.3 g/gCr (the severity of CKD is thus lowered from A3 to A2). Besides, it can also be checked whether a GFR of 25 mL/min/1.73 m$^2$ is increased to 35 mL/min/1.73 m$^2$ (the severity of CKD is thus lowered from G4 to G3b).

The inventive compound (I) or a pharmacologically acceptable salt thereof can delay transition to renal replacement therapy in a patient with chronic kidney disease at pre-dialysis stage.

In the present invention, the term "conservative treatment of chronic kidney disease" refers, in a patient having been diagnosed as having chronic kidney disease, to preventing the gradually deteriorating renal function after the diagnosis from further deteriorating by reducing the burden on the kidney having deteriorated function, or by reducing damage to other organs caused by the deteriorated renal function.

In the present invention, the term "delay transition to renal replacement therapy in a patient with chronic kidney disease at pre-dialysis stage" refers to extending the period until a criterion for introducing hemodialysis, introducing peritoneal dialysis or practicing preemptive kidney transplant is satisfied. For example, in the case of a chronic kidney disease patient for which it is planned to introduce peritoneal dialysis, it refers to extending the period until GFR, which is used as a criterion for the introduction, is lowered to about 6 mL/min/1.73 m$^2$ The inventive compound (I) or a pharmacologically acceptable salt thereof, or a crystalline form thereof, can suppress worsening of residual renal function in a patient after transition to renal replacement therapy. In the present invention, the term "worsening of residual renal function in a patient after transition to renal replacement therapy" refers to, for example, decreasing the urine amount per day after introducing dialysis as compared with that before the introduction, and specifically, decreasing the urine amount that was 400 mL or more per day before introducing peritoneal dialysis down to less than 400 mL. The worsening of residual renal function can be evaluated also by measuring creatinine clearance or a Kt/V value {(urea concentration in urine)/(urea concentration in the blood)×(urine amount per day)×7 days}.

In the present invention, the term "suppress worsening of residual renal function in a patient after transition to renal replacement therapy" refers to avoiding anuria. For example, when peritoneal dialysis (PD) is practiced before hemodialysis (HD) for the purpose of maintaining and not reducing a urine amount of 20 mL/day for 6 months to 1 year, or further maintaining remaining renal function, it can be checked whether or not a period of the PD before transition to the HD can be further extended.

An example of a dosage form of the inventive compound (I) or a pharmacologically acceptable salt thereof, or a crystalline form thereof, includes oral administration with a tablet, a granule, a powder, a capsule or a syrup.

Examples of an oral pharmaceutical form of the inventive compound (I) or a pharmacologically acceptable salt thereof, or a crystalline form thereof, include a tablet (including an orally disintegrating tablet), a pill, a granule, a powder, a capsule, a solution (including a spray), a suspension, an emulsion, a syrup, a paste and an elixir. A pharmaceutical in such a form can be prepared in accordance with a usual method by using an additive appropriately selected, if necessary, from pharmaceutically acceptable additives such as an excipient, a binder, a diluent, a stabilizer, a preservative, a colorant, a dissolution assisting agent, a suspending agent, a buffer or a humectant.

The dose of a formulation of the present invention is varied depending on the symptom, the age, the weight and the like, and is 0.1 to 1000 mg, preferably 1 to 300 mg, per adult once or several times a day. The formulation of the present invention can be administered to a non-human mammal.

The inventive compound (I) or a pharmacologically acceptable salt thereof, or a crystalline form thereof, can be used together with another drug. Examples of concomitant drugs that can be used include an angiotensin II receptor antagonist, an angiotensin-converting enzyme inhibitor, a calcium antagonist and a diuretic used in drug therapy of chronic kidney disease patients, and a cardiovascular drug such as a spherical carbonaceous adsorbent, and can be a large number of oral drugs including those prescribed based on a comorbid disease and the primary disease, such as a therapeutic drug for hyperuricemia, a therapeutic drug for hyperlipidemia, a therapeutic drug for diabetes, a steroid/immunosuppressive agent, an antiplatelet drug/anticoagulation drug, a therapeutic drug for hyperphosphatemia, an erythropoiesis stimulating factor preparation, an analgesic, an antiarrhythmic drug, an antidepressant, a therapeutic drug for dementia of Alzheimer type, a Parkinson's disease drug, a proton pump inhibitor (PPI), an antiallergic agent, an antibacterial and an OTC pharmaceutical.

The "angiotensin II receptor antagonist" corresponds to losartan, candesartan, valsartan, telmisartan, olmesartan, irbesartan, azilsartan and the like.

The "angiotensin-converting enzyme inhibitor" corresponds to captopril, enalapril, alacepril, delapril, cilazapril, lisinopril, benazepril, imidapril, temocapril, quinapril, trandolapril, perindopril erbumine and the like.

The "calcium antagonist" corresponds to nifedipine, amlodipine, efonidipine, cilnidipine, nicardipine, nisoldipine, nitrendipine, nilvadipine, barnidipine, felodipine, benidipine, manidipine, azelnidipine, aranidipine, diltiazem and the like.

The "diuretic" corresponds to trichlormethiazide, benzylhydrochlorothiazide, hydrochlorothiazide, meticrane, indapamide, tripamide, mefruside, furosemide, triamteren and the like.

Besides, the inventive compound (I) or a pharmacologically acceptable salt thereof, or a crystalline form thereof, can be formed into a combination drug with any of the above-described therapeutic drugs to be concomitantly used. A blending ratio with the concomitant drug can be arbitrarily set, and usually the blending ratio between the inventive compound or a pharmacologically acceptable salt thereof and the therapeutic drug to be concomitantly used is, in a weight ratio, usually 1:0.0001 to 200, and particularly preferably 1:0.001 to 10.

The present invention will now be described in more detail with reference to examples, test examples and formulation examples, and it is noted that the scope of the present invention is not limited to these examples.

Examples

The present invention will now be described in more detail with reference to examples and test examples, and it is noted that the scope of the present invention is not limited to these examples.

Elution in column chromatography in each example was performed under observation by TLC (thin layer chromatography). In the TLC observation, silica gel 60F$_{254}$ manufactured by Merck was used as a TLC plate, the solvent used as an elution solvent in column chromatography was used as a developing solvent, and a UV detector was employed as a detection method. For the column chromatography, an automated chromatograph (Purif-α2) manufactured by Shoko Scientific Co., Ltd. was used. The elution solvent was determined based on the TLC observation. For high-performance liquid chromatography, a preparative purification HPLC system manufactured by Gilson and columns manufactured by NOMURA CHEMICAL CO., LTD. (Develosil Combi-RP-5 28×100) were used.

Abbreviations used in the examples have meanings as follows:
DMF: N,N-Dimethylformamide
THF: Tetrahydrofuran
HATU: O-(7-Azabenzotriazol-1-yl)-N,N,N',N'-tetramethyluronium hexafluorophosphate
Me: Methyl
Boc: tert-Butoxycarbonyl In the examples described below, nuclear magnetic resonance (hereinafter referred to as $^1$H NMR) spectra were indicated in δ values (ppm) in terms of chemical shift values with tetramethylsilane used as a reference material. Splitting patterns were represented by s for singlet, d for doublet, t for triplet, q for quartet, m for multiplet and br for broad.

Mass analysis (hereinafter referred to as MS) was carried out by an ESI (Electrospray Ionization) method.

Example 1

2-[(4-Aminobenzoyl)amino]-2-ethylbutanoic Acid

[Formula 16]

(1a)

Methyl 2-({4-[(tert-butoxycarbonyl)amino]benzoyl}amino)-2-ethylbutanoate

[Formula 17]

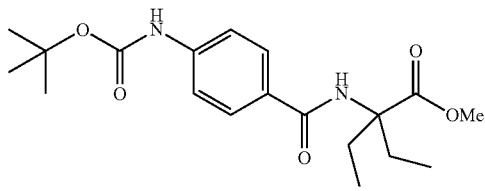

To a solution of 4-[(tert-butoxycarbonyl)amino]benzoic acid (CAS Registry Number 66493-39-8) (360 mg, 1.52 mmol) in DMF (5 mL), methyl 2-amino-2-ethylbutanoate (CAS Registry Number: 70974-26-4) (200 mg, 1.38 mmol), triethylamine (700 mg, 6.92 mmol) and HATU (540 mg, 1.42 mmol) were added, followed by stirring at room temperature overnight. After completion of the reaction, ethyl acetate was added to the reaction solution, an organic layer was separated, and then, the obtained organic layer was washed with water and dried over anhydrous sodium sulfate. A residue obtained through filtration and concentration of the filtrate under reduced pressure was purified by silica gel column chromatography [elution solvent: n-hexane/ethyl acetate=100/0-0/100 (V/V)] to obtain 480 mg (87%) of the title compound in the form of a solid. MS m/z: 365 (M+H)$^+$.

(1b)

Methyl 2-[(4-aminobenzoyl)amino]-2-ethylbutanoate

[Formula 18]

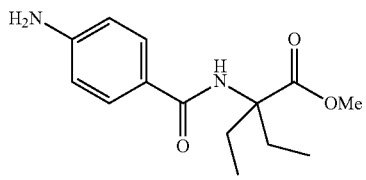

To a solution of the methyl 2-({4-[(tert-butoxycarbonyl)amino]benzoyl}amino)-2-ethylbutanoate (480 mg, 1.32 mmol) obtained in Example 1a in dichloromethane (5 mL), a 4N hydrochloric acid-ethyl acetate solution (15 mL, 60 mmol) was added, followed by stirring at room temperature for 3 hours. After completion of the reaction, water was added to the reaction solution, followed by diluting with ethyl acetate and neutralizing with sodium hydrocarbon. An organic layer was washed with water and dried over anhydrous sodium sulfate. A residue obtained through filtration and concentration under reduced pressure was purified by silica gel column chromatography [elution solvent: n-hexane/ethyl acetate=100/0-0/100 (V/V)] to obtain 350 mg (quantitative yield) of the title compound in the form of a solid.

MS m/z: 265 (M+H)$^+$.

(1c)

2-[(4-Aminobenzoyl)amino]-2-ethylbutanoic Acid

[Formula 19]

To a solution of the methyl 2-[4-aminobenzoyl)amino]-2-ethylbutanoate (350 mg, 1.32 mmol) obtained in Example 1b in methanol (10 mL), a 1N sodium hydroxide solution (5 mL, 5 mmol) was added, followed by heating at 70° C. for 12 hours. After completion of the reaction, the solvent of the reaction solution was distilled off under reduced pressure, and the obtained residue was neutralized with dilute hydrochloric acid. A solid produced was filtered with water, and washed with ethyl acetate to obtain the title compound (100 mg, 30%) in the form of a solid.
MS m/z: 251 (M+H)⁺.

Example 2

2-[(4-Amino-3-methylbenzoyl)amino]-2-ethylbutanoic Acid

[Formula 20]

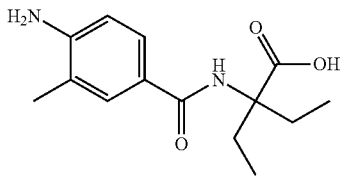

In the same manner as in Example 1, 400 mg (72%, 3 steps) of the title compound was obtained in the form of a solid from 4-[(tert-butoxycarbonyl)amino]-3-methylbenzoic acid (CAS Registry Number 180976-94-7) (510 mg, 2.03 mmol) and methyl 2-amino-2-ethylbutanoate (330 mg, 2.27 mmol).
MS m/z: 265 (M+H)⁺.

Example 3

2-[(4-Amino-3,5-dimethylbenzoyl)amino]-2-ethylbutanoic Acid

[Formula 21]

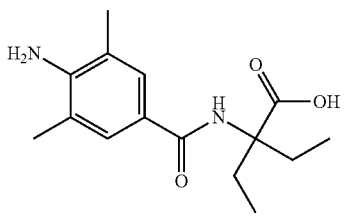

(3a)

Methyl 2-([3,5-dimethyl-4-nitrobenzoyl]amino)-2-ethylbutanoate

[Formula 22]

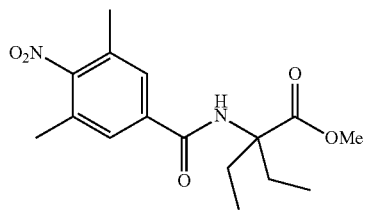

To a solution of 3,5-dimethyl-4-nitrobenzoic acid (CAS Registry Number 3095-38-3) (390 mg, 2.00 mmol) in DMF (6 mL), methyl 2-amino-2-ethylbutanoate (CAS Registry Number 70974-26-4) (330 mg, 2.27 mmol), triethylamine (1.4 g, 14 mmol) and HATU (1 g, 2.63 mmol) were added, followed by stirring at room temperature overnight. After completion of the reaction, ethyl acetate was added to the reaction solution, an organic layer was separated, and then the obtained organic layer was washed with water and dried over anhydrous sodium sulfate. A residue obtained through filtration and concentration under reduced pressure was purified by silica gel column chromatography [elution solvent: n-hexane/ethyl acetate=100/0-0/100 (V/V)] to obtain 600 mg (93%) of the title compound in the form of a solid.
MS m/z: 323 (M+H)⁺.

(3b)

Methyl 2-[(4-amino-3,5-dimethylbenzoyl)amino]-2-ethylbutanoate

[Formula 23]

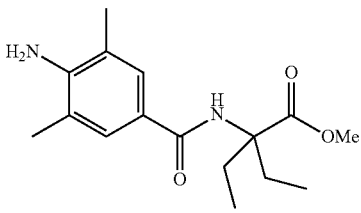

To a solution of the methyl 2-([3,5-dimethyl-4-nitrobenzoyl]amino)-2-ethylbutanoate (600 mg, 1.86 mmol) obtained in Example 3a in methanol (20 mL), 10% palladium-carbon (50 mg) was added, followed by vigorously stirring at room temperature for 3 hours under a hydrogen atmosphere. The reaction solution was filtered through celite to remove the catalyst, and a residue obtained through concentration of the filtrate under reduced pressure was purified by silica gel column chromatography [elution solvent: n-hexane/ethyl acetate=95/5-0/100 (V/V)] to obtain 540 mg (99%) of the title compound in the form of a solid.
MS m/z: 293 (M+H)⁺.

(3c)

2-[(4-Amino-3,5-dimethylbenzoyl)amino]-2-ethylbutanoic Acid

[Formula 24]

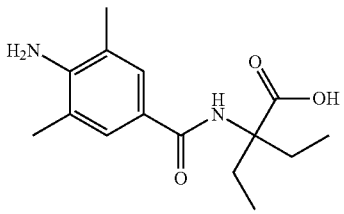

In the same manner as in Example 1c, 420 mg (82%) of the title compound was obtained in the form of a solid from the methyl 2-[(4-amino-3,5-dimethylbenzoyl)amino]-2-ethylbutanoate (540 mg, 1.85 mmol) obtained in Example 3b and a 1N sodium hydroxide solution (5 mL, 5 mmol).
MS m/z: 279 (M+H)⁺.

Example 4

2-[(4-Amino-3-methylbenzoyl)amino]-2-cyclopropyl butanoic Acid

[Formula 25]

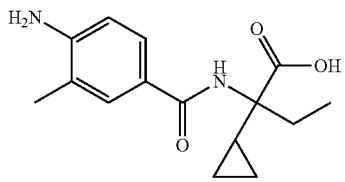

In the same manner as in Example 1, 360 mg (63%, 3 steps) of the title compound was obtained in the form of a solid from 4-[(tert-butoxycarbonyl)amino]-3-methylbenzoic acid (510 mg, 2.03 mmol) and methyl 2-amino-2-cyclopropyl butanoate hydrochloride (440 mg, 2.27 mmol).
MS m/z: 277 (M+H)$^+$.

Example 5

2-[(4-Amino-3-chlorobenzoyl)amino]-2-cyclopropyl butanoic Acid

[Formula 26]

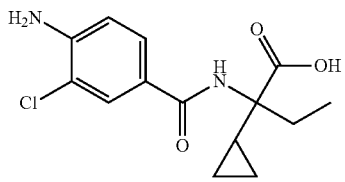

In the same manner as in Example 1, 410 mg (66%, 3 steps) of the title compound was obtained in the form of a solid from 4-[(tert-butoxycarbonyl)amino]-3-chlorobenzoic acid (CAS Registry Number 1340354-00-8) (550 mg, 2.02 mmol) and methyl 2-amino-2-cyclopropyl butanoate hydrochloride (440 mg, 2.27 mmol).
MS m/z: 297, 299 (M+H)$^+$.

Example 6

2-[(4-Amino-5-chloro-2-methoxybenzoyl)amino]-2-ethylbutanoic Acid

[Formula 27]

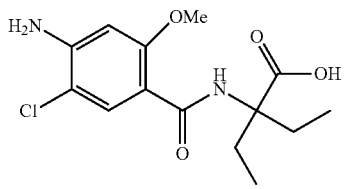

In the same manner as in Example 1, 430 mg (66%, 3 steps) of the title compound was obtained in the form of a solid from 4-[(tert-butoxycarbonyl)amino]-5-chloro-2-methoxybenzoic acid (CAS Registry Number 1155137-33-9) (610 mg, 2.02 mmol) and methyl 2-amino-2-ethylbutanoate (330 mg, 2.27 mmol). The thus obtained solid was crystalline.

$^1$H-NMR (400 MHz, CD$_3$OD) δ: 0.78 (7H, t, J=7.7 Hz), 1.84-1.90 (2H, m), 2.46-2.55 (2H, m), 3.96 (3H, s), 6.52 (1H, s), 7.79 (1H, s), 9.05 (1H, s).
MS m/z: 315, 317 (M+H)+.

A powder X-ray diffraction pattern of the crystals obtained through irradiation with copper Kα radiation (λ=1.54 angstroms, scanning speed=20°/min) is illustrated in FIG. 1. Peaks each having relative intensity, calculated by assuming that the maximum peak intensity is 100, of 14 or more in FIG. 1 are shown in Table 1.

TABLE 1

| Peak No. | 2θ (°) | d Value (Å) | Relative Intensity | Peak No. | 2θ (°) | d Value (Å) | Relative Intensity |
|---|---|---|---|---|---|---|---|
| 1 | 7.00 | 12.62 | 40 | 6 | 17.36 | 5.10 | 100 |
| 2 | 12.38 | 7.14 | 34 | 7 | 24.08 | 3.69 | 35 |
| 3 | 13.06 | 6.77 | 33 | 8 | 26.04 | 3.42 | 21 |
| 4 | 15.82 | 5.60 | 14 | 9 | 27.94 | 3.19 | 17 |
| 5 | 16.32 | 5.43 | 27 | 10 | 30.10 | 2.97 | 14 |

2-[(4-Amino-3-chloro-5-fluorobenzoyl)amino]-2-ethylbutanoic Acid

[Formula 28]

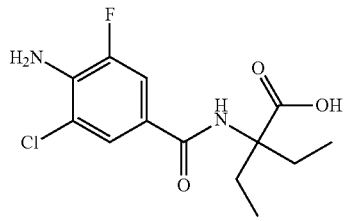

(7a)

Methyl 4-[bis(tert-butoxycarbonyl)amino]-3-chloro-5-fluorobenzoate

[Formula 29]

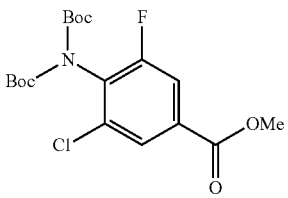

To a solution of 4-amino-3-chloro-5-fluorobenzoic acid (CAS Registry Number 1427420-66-3) (600 mg, 2.95 mmol) in dichloromethane (30 mL), di-tert-butyl dicarbonate (2 g, 9.16 mmol), 4-dimethylaminopyridine (120 mg, 0.98 mmol) and triethylamine (1.4 g, 14 mmol) were added, followed by stirring at room temperature. After completion of the reaction, a residue obtained through concentration of the reaction solution under reduced pressure was purified by silica gel chromatography [elution solvent: n-hexane/ethyl acetate=100/0-0/100 (V/V)] to obtain 1.15 g (97%) of the title compound in the form of a solid.

(7b)

4-[(tert-Butoxycarbonyl)amino]-3-chloro-5-fluorobenzoic Acid

[Formula 30]

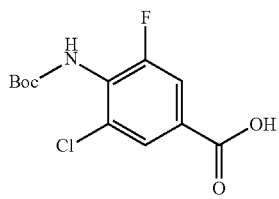

To a mixed solution of the methyl 4-[bis(tert-butoxycarbonyl)amino]-3-chloro-5-fluorobenzoate (1.15 g, 2.85 mmol) obtained in Example 7a in methanol (15 mL)-THF (10 mL), a 1N sodium hydroxide solution (20 mL, 20 mmol) was added, followed by heating at 70° C. for 6 hours. After completion of the reaction, the solvent of the reaction solution was distilled off under reduced pressure, and the resultant was diluted with water, acidified with dilute hydrochloric acid and extracted with ethyl acetate. The thus obtained extract was dried over anhydrous sodium sulfate, filtered and concentrated under reduced pressure to obtain 800 mg (97%) of the title compound in the form of a solid.

(7c)

2-[(4-Amino-3-chloro-5-fluorobenzoyl)amino]-2-ethylbutanoic Acid

[Formula 31]

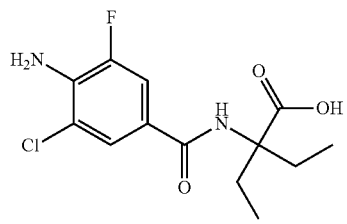

In the same manner as in Example 1, 220 mg (35%, 3 steps) of the title compound was obtained in the form of a solid from 4-[(tert-butoxycarbonyl)amino]-3-chloro-5-fluorobenzoic acid (580 mg, 2.00 mmol) and methyl 2-amino-2-ethylbutanoate (330 mg, 2.27 mmol).
MS m/z: 303, 305 (M+H)$^+$.

Example 8

N-(4-Amino-5-chloro-2-ethoxybenzoyl)-2-methylalanine

[Formula 32]

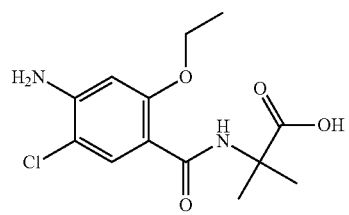

In the same manner as in Example 1, 480 mg (77%, 3 steps) of the title compound was obtained in the form of a solid from 4-[(tert-butoxycarbonyl)amino]-5-chloro-2-ethoxybenzoic acid (CAS Registry Number 636582-68-8) (630 mg, 2.00 mmol) and ethyl 2-methylalanine hydrochloride (CAS Registry Number 17288-15-2) (500 mg, 2.98 mmol).
MS m/z: 301, 303 (M+H)$^+$.

Example 9

N-[4-Amino-5-chloro-2-(propan-2-yloxy)benzoyl]-2-methylalanine

[Formula 33]

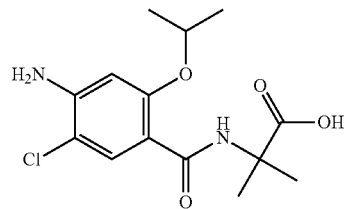

(9a)

Methyl 4-amino-5-chloro-2-(propan-2-yloxy)benzoate

[Formula 34]

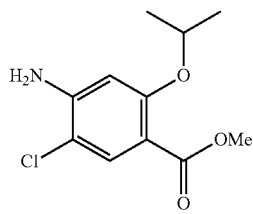

To a solution of methyl 4-amino-2-(propan-2-yloxy)benzoate (CAS Registry Number 909563-22-0) (2.33 g, 11.1 mmol) in ethyl acetate (25 mL), N-chlorosuccinimide (1.5 g, 11 mmol) was added, followed by heating at 50° C. After completion of the reaction, a residue obtained through concentration of the reaction solution under reduced pressure was purified by silica gel column chromatography [elution solvent: n-hexane/ethyl acetate=100/0-0/100 (V/V)] to obtain 2.7 g (quantitative yield) of the title compound in the form of a solid.

MS m/z: 244, 246 (M+H)⁺.

(9b)

4-[(tert-Butoxycarbonyl)amino]-5-chloro-2-(propan-2-yloxy)benzoic Acid

[Formula 35]

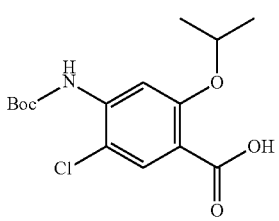

In the same manner as in Examples 7a and 7b, 2.36 g (65%, 2 steps) of the title compound was obtained in the form of a solid from the methyl 4-amino-5-chloro-2-(propan-2-yloxy)benzoate (2.7 g, 11 mmol) obtained in Example 9a.

MS m/z: 330, 332 (M+H)⁺.

(9c)

N-(4-Amino-5-chloro-2-(propan-2-yloxy)benzoyl)-2-methylalanine

[Formula 36]

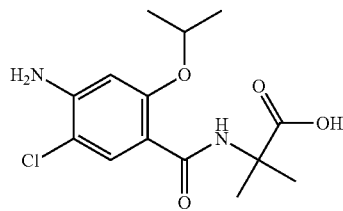

In the same manner as in Example 1, 360 mg (57%, 3 steps) of the title compound was obtained in the form of a solid from the 4-[(tert-butoxycarbonyl)amino]-5-chloro-2-(propan-2-yloxy)benzoic acid (660 mg, 2.00 mmol) obtained in Example 9b and methyl 2-methylalanine hydrochloride (CAS Registry Number 15028-41-8) (330 mg, 2.15 mmol).

MS m/z: 315, 317 (M+H)+.

Example 10

(−)-N-(4-Amino-5-chloro-2-methoxybenzoyl)-D-isovaline

[Formula 37]

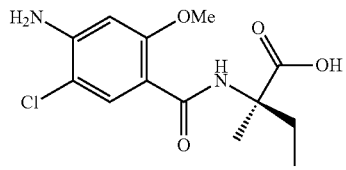

To a suspension of 4-amino-5-chloro-2-methoxybenzoic acid (CAS Registry Number 7206-70-4) (1 g, 4.96 mmol) and triethylamine (1.4 mL, 9.92 mmol) in DMF (4.96 mL), HATU (1.89 g, 4.96 mmol) was added, followed by stirring at room temperature for 1 hour. (R)-α-Ethylalanine monohydrate (697 mg, 5.16 mmol) was added thereto, followed by stirring at 50° C. for 3 hours. Water (100 mL) was added thereto and sonication was performed for 12 hours. A solid produced was filtered and washed with water and dried under reduced pressure to obtain 1.26 g of a crude product. Acetonitrile (200 mL) was added to 1.1 g of the thus obtained crude product and heated to reflux.

A solid produced through dissolution and leaving the mixture at room temperature for 24 hours was filtered and washed with acetonitrile to obtain a solid (0.72 g). The thus obtained solid was purified by HPLC [elution solvent: 0.1% formic acid-containing aqueous solution/0.1% formic acid-containing acetonitrile=74/26-46/54 (V/V)] to obtain 0.49 g (33%) of the title compound in the form of a solid. The thus obtained solid was crystalline.

¹H-NMR (400 MHz, CD₃OD) δ: 0.84 (3H, t, J=7.6 Hz), 1.64 (3H, s), 1.87-1.96 (1H, m), 2.27-2.36 (1H, m), 3.94 (3H, s), 6.30 (1H, s), 8.10 (1H, s), 8.23 (1H, br s).

MS m/z: 301, 303 [M+H]⁺.

$[\alpha]_D^{25}$ −19.82° (c 0.5, Methanol).

Figure 2:
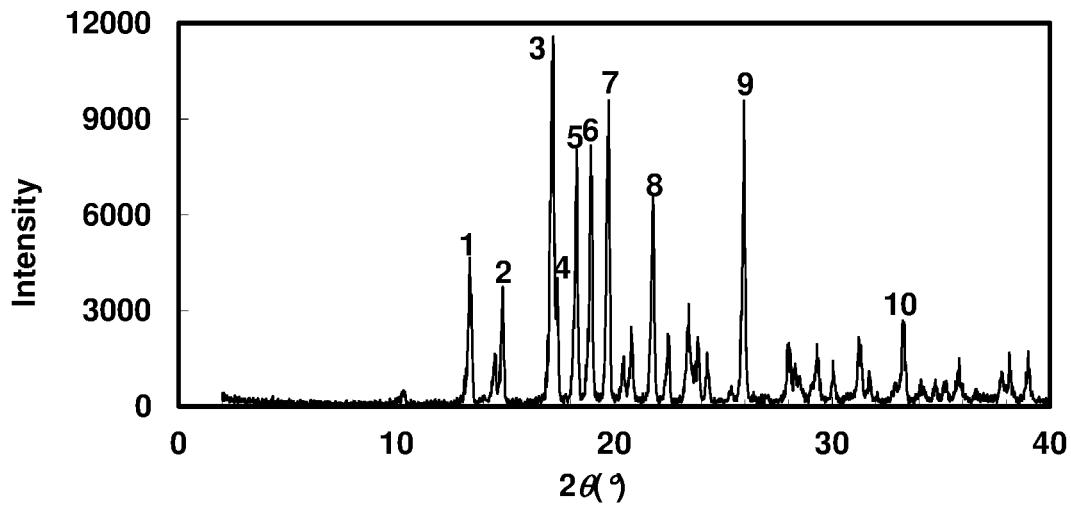
FIG. 2 is a powder X-ray diffraction diagram of crystals obtained in Example 10. The ordinate indicates diffraction intensity in count/sec. (cps), and the abscissa indicates a value of diffraction angle 2θ.

A powder X-ray diffraction pattern of the crystals obtained through irradiation with copper K radiation (λ=1.54 angstroms, scanning speed=20°/min) is illustrated in FIG. 2. Peaks each having relative intensity, calculated by assuming that the maximum peak intensity is 100, of 22 or more in FIG. 2 are shown in Table 2.

TABLE 2

| Peak No. | 2θ (°) | d Value (Å) | Relative Intensity | Peak No. | 2θ (°) | d Value (Å) | Relative Intensity |
|---|---|---|---|---|---|---|---|
| 1 | 13.38 | 6.61 | 38 | 6 | 18.94 | 4.68 | 69 |
| 2 | 14.86 | 5.96 | 32 | 7 | 19.72 | 4.50 | 75 |
| 3 | 17.16 | 5.16 | 100 | 8 | 21.78 | 4.08 | 61 |
| 4 | 17.38 | 5.10 | 30 | 9 | 25.94 | 3.43 | 75 |
| 5 | 18.26 | 4.85 | 69 | 10 | 33.26 | 2.69 | 22 |

(−)-N-(4-Amino-5-chloro-2-ethoxybenzoyl)-D-isovaline

[Formula 38]

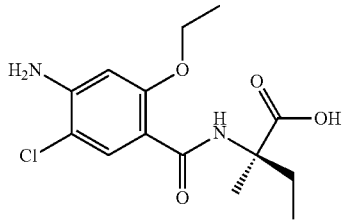

To a suspension of 4-amino-5-chloro-2-ethoxybenzoic acid (CAS Registry Number 108282-38-8) (230 mg, 1.1 mmol), triethylamine (0.3 mL, 2.1 mmol) and (R)-α-ethylalanine monohydrate (150 mg, 1.1 mmol) in DMF (2.1 mL), HATU (450 mg, 1.2 mmol) was added, followed by stirring at 50° C. for 5 hours. After completion of the reaction, the reaction solution was diluted with DMSO and purified by HPLC [elution solvent: 0.1% formic acid-containing aqueous solution/0.1% formic acid-containing acetonitrile=74/26-47/53 (V/V)] to obtain 250 mg (74%) of the title compound in the form of a solid. The thus obtained solid was crystalline.

$^1$H-NMR (400 MHz, CD$_3$OD) δ: 0.85 (3H, t, J=7.3 Hz), 1.52 (3H, t, J=7.0 Hz), 1.64 (3H, s), 1.87-1.96 (1H, m), 2.26-2.35 (1H, m), 4.16 (2H, q, J=6.9 Hz), 6.49 (1H, s), 7.79 (1H, s), 8.83 (1H, s).
MS m/z: 315, 317 [M+H]+.
$[α]_D^{25}$ −19.44° (c 0.5, Methanol).

Figure 3:
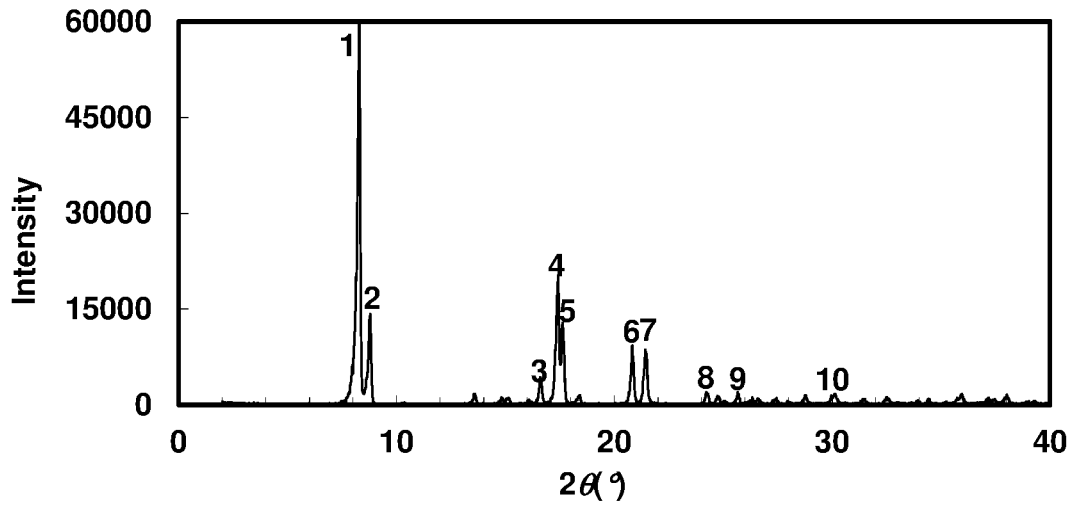
FIG. 3 is a powder X-ray diffraction diagram of crystals obtained in Example 11. The ordinate indicates diffraction intensity in count/sec. (cps), and the abscissa indicates a value of diffraction angle 2θ.

A powder X-ray diffraction pattern of the crystals obtained through irradiation with copper Kα radiation (λ=1.54 angstroms, scanning speed=20°/min) is illustrated in FIG. 3. Peaks each having relative intensity, calculated by assuming that the maximum peak intensity is 100, of 3 or more in FIG. 3 are shown in Table 3.

TABLE 3

| Peak No. | 2θ (°) | d Value (Å) | Relative Intensity | Peak No. | 2θ (°) | d Value (Å) | Relative Intensity |
|---|---|---|---|---|---|---|---|
| 1 | 8.28 | 10.67 | 100 | 6 | 20.84 | 4.26 | 14 |
| 2 | 8.78 | 10.06 | 23 | 7 | 21.44 | 4.14 | 14 |
| 3 | 16.62 | 5.33 | 7 | 8 | 24.24 | 3.67 | 4 |
| 4 | 17.40 | 5.09 | 32 | 9 | 25.68 | 3.47 | 3 |
| 5 | 17.64 | 5.02 | 20 | 10 | 30.12 | 2.96 | 3 |

Example 12

(+)-N-(4-Amino-5-chloro-2-methoxybenzoyl)-L-isovaline

[Formula 39]

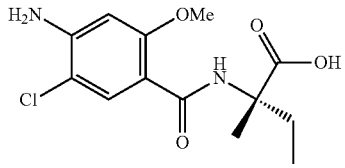

To a suspension of 4-amino-5-chloro-2-methoxybenzoic acid (310 mg, 0.50 mmol), triethylamine (0.43 mL, 3.1 mmol) and (S)-α-ethylalanine monohydrate (200 mg, 1.5 mmol) in DMF (1.5 mL), HATU (700 mg, 1.8 mmol) was added, followed by stirring at 50° C. for 2 hours. After completion of the reaction, the reaction solution was diluted with DMSO and purified by HPLC [elution solvent: 0.1% formic acid-containing aqueous solution/0.1% formic acid-containing acetonitrile=73/27-45/55 (V/V)] to obtain 450 mg (45%) of the title compound in the form of a solid.

$^1$H-NMR (400 MHz, CD$_3$OD) δ: 0.84 (3H, t, J=7.3 Hz), 1.64 (3H, s), 1.87-1.96 (1H, m), 2.27-2.36 (1H, m), 3.95 (3H, s), 6.52 (1H, s), 7.79 (1H, s).
MS m/z: 301, 303 [M+H]+.
$[α]_D^{25}$ +20.73° (c 0.5, Methanol).

Example 13

(+)-N-(4-Amino-5-chloro-2-ethoxybenzoyl)-L-isovaline

[Formula 40]

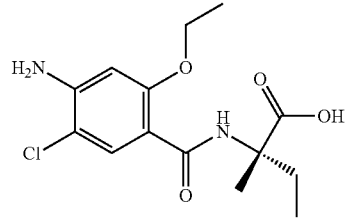

To a suspension of 4-amino-5-chloro-2-ethoxybenzoic acid (330 mg, 1.5 mmol), triethylamine (0.42 mL, 3.1 mmol) and (S)-α-ethylalanine monohydrate (200 mg, 1.5 mmol) in DMF (1.5 mL), HATU (700 mg, 1.8 mmol) was added, followed by stirring at 50° C. for 2 hours. The reaction solution was diluted with DMSO and purified by HPLC [elution solvent: 0.1% formic acid-containing aqueous solution/0.1% formic acid-containing acetonitrile=70/30-42/58 (V/V)] to obtain 310 mg (64%) of the title compound in the form of a solid.

$^1$H-NMR (400 MHz, CD$_3$OD) δ: 0.85 (3H, t, J=7.3 Hz), 1.52 (3H, t, J=7.0 Hz), 1.64 (3H, s), 1.87-1.96 (1H, m), 2.26-2.35 (1H, m), 4.15 (2H, q, J=6.9 Hz), 6.50 (1H, s), 7.80 (1H, s).
MS m/z: 315, 317 [M+H]+.
$[α]_D^{25}$ +22.47° (c 0.5, Methanol).

Example 14

N-(4-Amino-5-chloro-2-propoxybenzoyl)-2-methylalanine

[Formula 41]

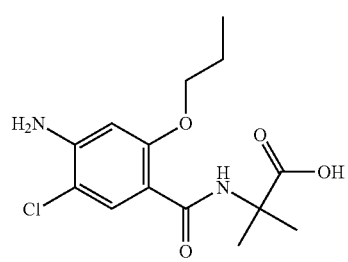

(14a)

Propyl 4-nitro-2-propoxybenzoate

[Formula 42]

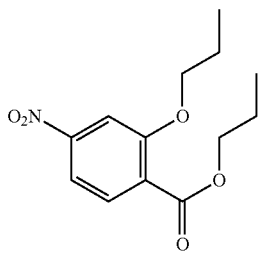

To a suspension of 2-hydroxy-4-nitrobenzoic acid (CAS Registry Number 619-19-2) (1.0 g, 5.5 mmol) and 1-iodopropane (1.8 mL, 18 mmol) in DMF (5.5 mL), potassium carbonate (2.6 g, 19 mmol) was added, followed by stirring at 70° C. for 12 hours. After completion of the reaction, the reaction solution was cooled to room temperature, water was added thereto, and the resultant was extracted with n-hexane. An organic layer was dried over anhydrous sodium sulfate and filtered, and the filtrate was concentrated under reduced pressure to obtain 1.5 g (quantitative yield) of the title compound.

$^1$H-NMR (400 MHz, CDCl$_3$) δ: 1.03 (3H, t, J=7.3 Hz), 1.09 (3H, t, J=7.6 Hz), 1.78-1.80 (2H, m), 1.88-1.92 (2H, m), 4.09 (2H, t, J=6.7 Hz), 4.30 (2H, t, J=6.7 Hz), 7.80-7.86 (3H, m).

(14b)

Propyl 4-amino-2-propoxybenzoate

[Formula 43]

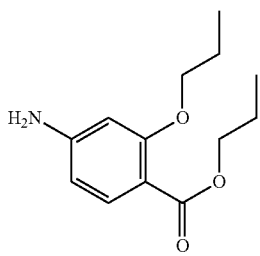

To a solution of the propyl 4-nitro-2-propoxybenzoate (1.5 g, 5.61 mmol) obtained in Example 14a in ethanol (10 mL), 10% palladium-carbon (100 mg) was added, followed by stirring at room temperature for 6 hours under a hydrogen atmosphere. After completion of the reaction, a residue obtained through filtration of the catalyst of the reaction solution and concentration of the filtrate under reduced pressure was purified by silica gel column chromatography [elution solvent: n-hexane/ethyl acetate=50/5-0/100 (V/V)] to obtain 1.33 g (quantitative yield) of the title compound.

(14c)

Propyl 4-amino-5-chloro-2-propoxybenzoate

[Formula 44]

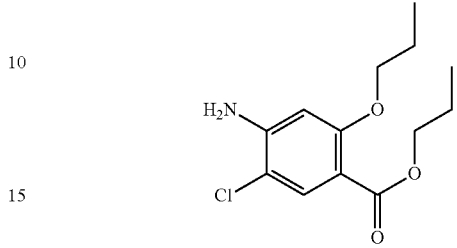

A solution of the propyl 4-amino-2-propoxybenzoate (1.07 g, 4.51 mmol) obtained in Example 14b in dichloromethane (10 mL) was cooled to 0° C. and a solution of Palau' Chlor (registered trademark, 851 mg, 4.06 mmol) in dichloromethane (10 mL) was added dropwise to the above solution over a period of 30 minutes. After completion of the reaction, a residue obtained through filtration of the reaction solution and concentration of the filtrate under reduced pressure was purified by silica gel column chromatography [elution solvent: n-hexane/ethyl acetate=85/15-50/50 (V/V)] to obtain 790 mg (64%) of the title compound.

$^1$H-NMR (400 MHz, CDCl$_3$) δ: 1.01 (3H, t, J=7.6 Hz), 1.06 (3H, t, J=7.3 Hz), 1.75 (2H, td, J=14.0, 7.3 Hz), 1.85 (2H, td, J=14.0, 7.3 Hz), 3.91 (2H, t, J=6.4 Hz), 4.20 (2H, t, J=6.7 Hz), 4.38 (2H, s), 6.27 (1H, s), 7.83 (1H, s).
MS m/z: 272, 274 [M+H]$^+$.

(14d)

4-Amino-5-chloro-2-propoxybenzoic Acid

[Formula 45]

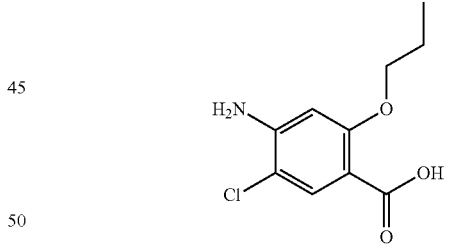

To a solution of the propyl 4-amino-5-chloro-2-propoxybenzoate (790 mg, 2.9 mmol) obtained in Example 14c in methanol/THF (3/1, 40 mL), a 1N sodium hydroxide solution (10 mL, 10 mmol) was added, followed by stirring at room temperature for 1 hour. Besides, a 5N sodium hydroxide solution (5 mL, 25 mmol) was added thereto, followed by stirring at 60° C. for 3 hours. After completion of the reaction, a solid produced by adjusting the pH of the reaction solution to 5 with 2N hydrochloric acid was filtered, washed with water, and dried under reduced pressure to obtain 650 mg (97%) of the title compound.

$^1$H-NMR (400 MHz, CD$_3$OD) δ: 1.06 (3H, t, J=7.6 Hz), 1.85 (2H, q, J=6.9 Hz), 4.04 (2H, t, J=6.4 Hz), 6.47 (1H, s), 7.75 (1H, s).
MS m/z: 230, 232 [M+H]+.

(14e)

N-(4-Amino-5-chloro-2-propoxybenzoyl)-2-methyl-alanine

[Formula 46]

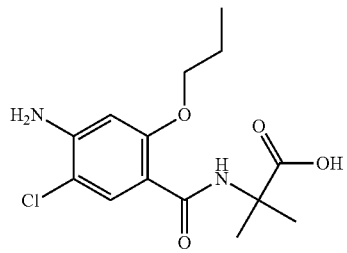

In the same manner as in Example 1, 70 mg (75%) of the title compound was obtained in the form of a solid from the 4-amino-5-chloro-2-propoxybenzoic acid (100 mg, 0.44 mmol) obtained in Example 14d and methyl 2-methylalanine hydrochloride (CAS Registry Number 15028-41-8) (80 mg, 0.52 mmol).

$^1$H-NMR (400 MHz, CD$_3$OD) δ: 1.09 (3H, t, J=7.6 Hz), 1.60 (6H, s), 1.93 (2H, q, J=6.7 Hz), 4.06 (2H, t, J=6.4 Hz), 6.48 (1H, s), 7.78 (1H, s).
MS m/z: 315 [M+H]$^+$.

Example 15

(−)-N-(4-Amino-5-bromo-2-methoxybenzoyl)-D-isovaline

[Formula 47]

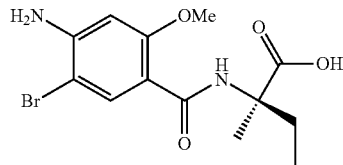

To a suspension of 4-amino-5-bromo-2-methoxybenzoic acid (CAS Registry Number 35290-97-2) (100 mg, 0.41 mmol), (R)-α-ethylalanine monohydrate (62 mg, 0.46 mmol) and triethylamine (0.11 mL, 0.81 mmol) in DMF (0.41 mL), HATU (190 mg, 0.49 mmol) was added, followed by stirring at 50° C. for 5 hours. After completion of the reaction, the reaction solution was diluted with DMSO and purified by HPLC [elution solvent: 0.1% formic acid-containing aqueous solution/0.1% formic acid-containing acetonitrile=74/26-46/54 (V/V)] to obtain 100 mg (71%) of the title compound in the form of a solid. The thus obtained solid was crystalline.

$^1$H-NMR (400 MHz, CD$_3$OD) δ: 0.84 (3H, t, J=7.3 Hz), 1.63 (3H, s), 1.95-1.86 (1H, m), 2.36-2.27 (1H, m), 3.95 (3H, s), 6.52 (1H, s), 7.95 (1H, s).
MS m/z: 345, 347 [M+H]$^+$.
$[\alpha]_D^{25}$ −18.34° (c 0.5, Methanol).

Figure 4:
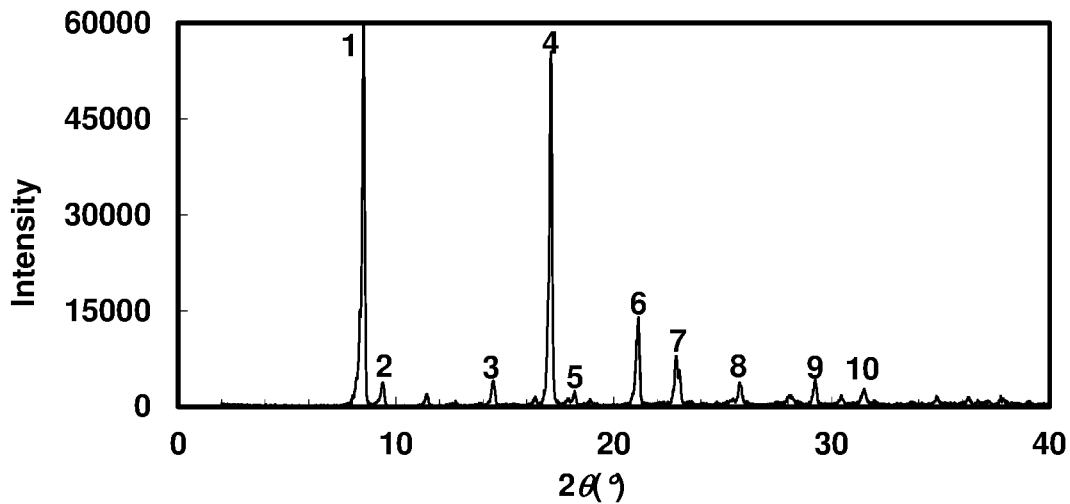
FIG. 4 is a powder X-ray diffraction diagram of crystals obtained in Example 15. The ordinate indicates diffraction intensity in count/sec. (cps), and the abscissa indicates a value of diffraction angle 2θ.

A powder X-ray diffraction pattern of the crystals obtained through irradiation with copper K radiation (λ=1.54 angstroms, scanning speed=20°/min) is illustrated in FIG. 4. Peaks each having relative intensity, calculated by assuming that the maximum peak intensity is 100, of 4 or more in FIG. 4 are shown in Table 4.

TABLE 4

| Peak No. | 2θ (°) | d Value (Å) | Relative Intensity | Peak No. | 2θ (°) | d Value (Å) | Relative Intensity |
|---|---|---|---|---|---|---|---|
| 1 | 8.52 | 10.37 | 100 | 6 | 21.12 | 4.20 | 23 |
| 2 | 9.40 | 9.40 | 7 | 7 | 22.86 | 3.89 | 13 |
| 3 | 14.46 | 6.12 | 7 | 8 | 25.78 | 3.45 | 7 |
| 4 | 17.12 | 5.18 | 92 | 9 | 29.26 | 3.05 | 7 |
| 5 | 18.22 | 4.87 | 4 | 10 | 31.50 | 2.84 | 5 |

Example 16

(−)-N-(4-Amino-5-iodo-2-methoxybenzoyl)-D-isovaline

[Formula 48]

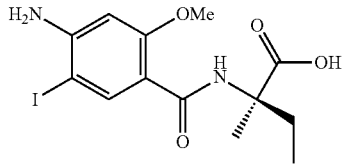

In the same manner as in Example 15, 95 mg (71%) of the title compound was obtained in the form of a solid from 4-amino-5-iodo-2-methoxybenzoic acid (CAS Registry Number 155928-39-5) (100 mg, 0.34 mmol) and (R)-α-ethylalanine monohydrate (52 mg, 0.38 mmol). The thus obtained solid was crystalline.

$^1$H-NMR (400 MHz, CD$_3$OD) δ: 0.84 (3H, t, J=7.3 Hz), 1.63 (3H, s), 1.95-1.86 (1H, m), 2.36-2.26 (1H, m), 3.94 (3H, s), 6.50 (1H, s), 8.17 (1H, s).
MS m/z: 393 [M+H]$^+$.
$[\alpha]_D^{25}$ −15.73° (c 0.5, Methanol).

Figure 5:
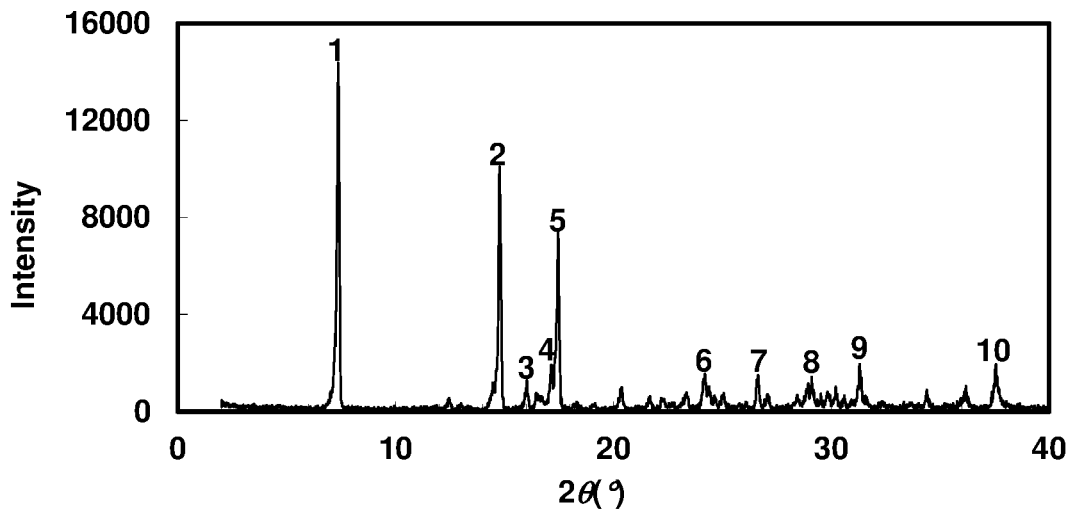
FIG. 5 is a powder X-ray diffraction diagram of crystals obtained in Example 16. The ordinate indicates diffraction intensity in count/sec. (cps), and the abscissa indicates a value of diffraction angle 2θ.

A powder X-ray diffraction pattern of the crystals obtained through irradiation with copper K radiation (λ=1.54 angstroms, scanning speed=20°/min) is illustrated in FIG. 5. Peaks each having relative intensity, calculated by assuming that the maximum peak intensity is 100, of 8 or more in FIG. 5 are shown in Table 5.

TABLE 5

| Peak No. | 2θ (°) | d Value (Å) | Relative Intensity | Peak No. | 2θ (°) | d Value (Å) | Relative Intensity |
|---|---|---|---|---|---|---|---|
| 1 | 7.36 | 12.00 | 100 | 6 | 24.18 | 3.68 | 11 |
| 2 | 14.78 | 5.99 | 71 | 7 | 26.62 | 3.35 | 11 |
| 3 | 16.02 | 5.53 | 8 | 8 | 29.12 | 3.06 | 9 |
| 4 | 17.14 | 5.17 | 14 | 9 | 31.30 | 2.86 | 13 |
| 5 | 17.46 | 5.08 | 49 | 10 | 37.56 | 2.39 | 14 |

(+)-N-(4-Amino-5-bromo-2-methoxybenzoyl)-L-isovaline

[Formula 49]

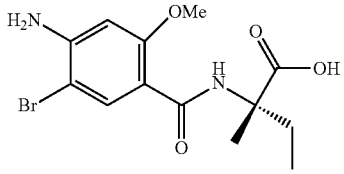

In the same manner as in Example 15, 63 mg (48%) of the title compound was obtained in the form of a solid from 4-amino-5-bromo-2-methoxybenzoic acid (94 mg, 0.38 mmol) and (S)-α-ethylalanine (49 mg, 0.42 mmol).

$^1$H-NMR (400 MHz, CD$_3$OD) δ: 0.84 (3H, t, J=7.3 Hz), 1.64 (3H, s), 1.96-1.86 (1H, m), 2.36-2.27 (1H, m), 3.95 (3H, s), 6.52 (1H, s), 7.95 (1H, s).
MS m/z: 345, 347 [M+H]$^+$.
$[α]_D^{25}$ +18.12° (c 0.5, Methanol)

Example 18

(+)-N-(4-Amino-5-iodo-2-methoxybenzoyl)-L-isovaline

[Formula 50]

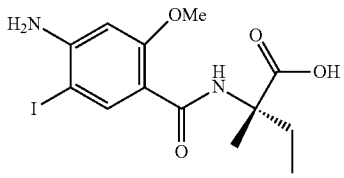

In the same manner as in Example 15, 66 mg (51%) of the title compound was obtained in the form of a solid from 4-amino-5-iodo-2-methoxybenzoic acid (97 mg, 0.33 mmol) and (S)-α-ethylalanine (43 mg, 0.36 mmol).

$^1$H-NMR (400 MHz, CD$_3$OD) δ: 0.84 (3H, t, J=7.3 Hz), 1.63 (3H, s), 1.95-1.86 (1H, m), 2.36-2.27 (1H, m), 3.94 (3H, s), 6.49 (1H, s), 8.16 (1H, s).
MS m/z: 393 [M+H]$^+$.
$[α]_D^{25}$ +16.17° (c 0.5, Methanol).

Example 19

(+)-N-(4-Amino-5-bromo-2-ethoxybenzoyl)-L-isovaline

[Formula 51]

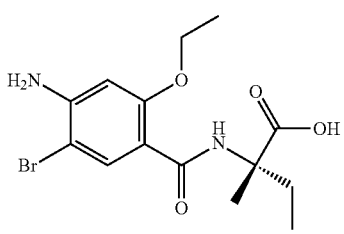

In the same manner as in Example 15, 65 mg (47%) of the title compound was obtained in the form of a solid from 4-amino-5-bromo-2-ethoxybenzoic acid (100 mg, 0.38 mmol) and (S)-α-ethylalanine (50 mg, 0.42 mmol).

$^1$H-NMR (400 MHz, DMSO-D$_6$) 1H-NMR (DMSO-D6) δ: 0.76 (3H, t, J=7.3 Hz), 1.44 (3H, t, J=7.0 Hz), 1.51 (3H, s), 1.83-1.74 (1H, m), 2.21-2.12 (1H, m), 4.09 (2H, q, J=7.1 Hz), 5.91 (1H, br s), 6.48 (1H, s), 7.85 (1H, s), 8.43 (1H, s), 12.82 (1H, br s).
MS m/z: 359, 361 [M+H]$^+$.
$[α]_D^{25}$ +20.45° (c 0.5, Methanol).

Example 20

(+)-N-(4-Amino-2-ethoxy-5-iodobenzoyl)-L-isovaline

[Formula 52]

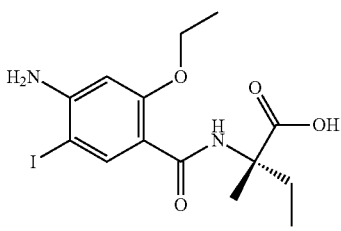

In the same manner as in Example 15, 43 mg (30%) of the title compound was obtained in the form of a solid from 4-amino-2-ethoxy-5-iodobenzoic acid (110 mg, 0.36 mmol) and (S)-α-ethylalanine (46 mg, 0.39 mmol).

$^1$H-NMR (400 MHz, DMSO-D$_6$) δ: 0.76 (3H, t, J=7.6 Hz), 1.44 (3H, t, J=7.0 Hz), 1.51 (3H, s), 1.74-1.83 (1H, m), 2.20-2.11 (1H, m), 4.08 (2H, q, J=6.9 Hz), 5.70 (1H, br s), 6.46 (1H, s), 8.06 (1H, s), 8.41 (1H, s).
MS m/z: 407 [M+H]$^+$.
$[α]_D^{25}$ +19.67° (c 0.5, Methanol).

Example 21

(−)-N-(4-Amino-5-bromo-2-ethoxybenzoyl)-D-isovaline

[Formula 53]

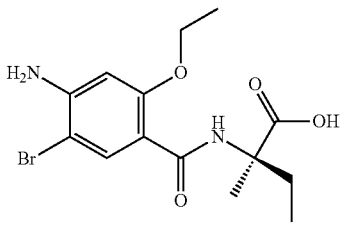

In the same manner as in Example 15, 110 mg (80%) of the title compound was obtained in the form of a solid from 4-amino-5-bromo-2-ethoxybenzoic acid (100 mg, 0.38 mmol) and (R)-α-ethylalanine monohydrate (59 mg, 0.44 mmol). The thus obtained solid was crystalline.

$^1$H-NMR (400 MHz, DMSO-D$_6$) δ: 0.76 (3H, t, J=7.3 Hz), 1.45 (3H, t, J=7.0 Hz), 1.51 (3H, s), 1.83-1.75 (1H, m), 2.21-2.12 (1H, m), 4.09 (2H, q, J=7.1 Hz), 6.49 (1H, s), 7.85 (1H, s), 8.43 (1H, s), 12.83 (1H, br s).

MS m/z: 359, 361 [M+H]$^+$.

$[\alpha]_D^{25}$ −20.79° (c 0.5, Methanol)

Figure 6:
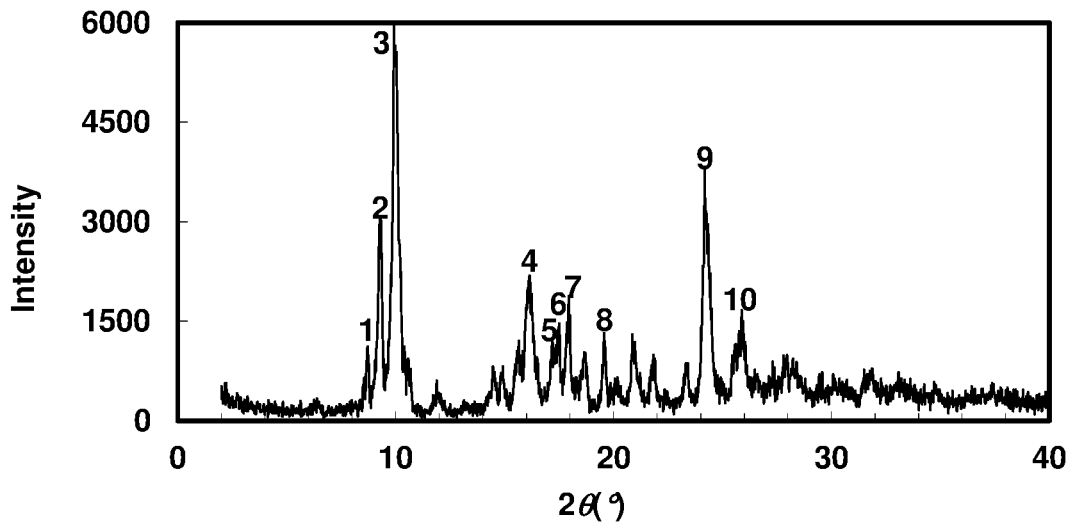
FIG. 6 is a powder X-ray diffraction diagram of crystals obtained in Example 21. The ordinate indicates diffraction intensity in count/sec. (cps), and the abscissa indicates a value of diffraction angle 2θ.

A powder X-ray diffraction pattern of the crystals obtained through irradiation with copper K radiation ($\lambda$=1.54 angstroms, scanning speed=20°/min) is illustrated in FIG. 6. Peaks each having relative intensity, calculated by assuming that the maximum peak intensity is 100, of 19 or more in FIG. 6 are shown in Table 6.

TABLE 6

| Peak No. | 2θ (°) | d Value (Å) | Relative Intensity | Peak No. | 2θ (°) | d Value (Å) | Relative Intensity |
|---|---|---|---|---|---|---|---|
| 1 | 8.70 | 10.16 | 19 | 6 | 17.48 | 5.07 | 24 |
| 2 | 9.28 | 9.52 | 53 | 7 | 17.92 | 4.95 | 27 |
| 3 | 9.98 | 8.86 | 100 | 8 | 19.58 | 4.53 | 20 |
| 4 | 16.12 | 5.49 | 36 | 9 | 24.22 | 3.67 | 57 |
| 5 | 17.18 | 5.16 | 19 | 10 | 25.92 | 3.43 | 26 |

Example 22

(−)-N-(4-Amino-2-ethoxy-5-iodobenzoyl)-D-isovaline

[Formula 54]

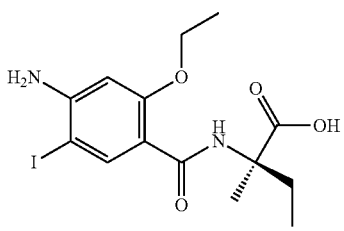

In the same manner as in Example 15, 100 mg (69%) of the title compound was obtained in the form of a solid from 4-amino-2-ethoxy-5-iodobenzoic acid (110 mg, 0.36 mmol) and (R)-α-ethylalanine monohydrate (55 mg, 0.41 mmol).

$^1$H-NMR (400 MHz, DMSO-D$_6$) δ: 0.76 (3H, t, J=7.6 Hz), 1.44 (6H, t, J=7.0 Hz), 1.51 (6H, s), 1.83-1.74 (1H, m), 2.20-2.11 (1H, m), 4.08 (2H, q, J=6.9 Hz), 5.63 (1H, br s), 6.46 (1H, s), 8.06 (1H, s), 8.41 (1H, s).

MS m/z: 407 [M+H]$^+$.

$[\alpha]_D$ −19.24° (c 0.5, Methanol)

Example 23

(−)-N-(4-Amino-2-ethoxy-5-fluorobenzoyl)-D-isovaline

[Formula 55]

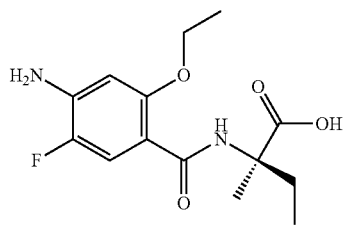

(23a)

Methyl 4-amino-2-ethoxy-5-fluorobenzoate

[Formula 56]

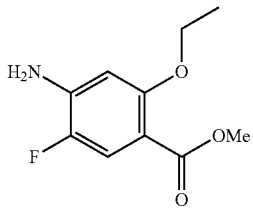

To a suspension of methyl 4-bromo-2-ethoxy-5-fluorobenzoate (CAS Registry Number 1823348-15-7) (1.12 g, 4.04 mmol), palladium acetate (907 mg, 0.404 mmol), 4,5-bis(diphenylphosphino)-9,9-dimethylxanthene (351 mg, 0.606 mmol) and cesium carbonate (2.63 g, 8.08 mmol) in 1,4-dioxane (20 mL), benzophenonimine (1.10 g, 6.06 mmol) was added, followed by stirring at 100° C. for 4 hours under a nitrogen atmosphere. After completion of the reaction, the reaction solution was cooled to room temperature, filtered and washed with n-hexane, and the filtrate was concentrated under reduced pressure. The thus obtained residue was dissolved in THF (5 mL), and 2N hydrochloric acid (5 mL, 10 mmol) was added thereto, followed by stirring at room temperature for 1 hour. The reaction solution was concentrated under reduced pressure, neutralized with saturated aqueous sodium hydrogen carbonate and extracted with ethyl acetate. The thus obtained extract was dried over anhydrous sodium sulfate and filtered, and the filtrate was concentrated under reduced pressure. The thus obtained residue was purified by silica gel column chromatography [elution solvent: n-hexane/ethyl acetate=80/20-50/50 (V/V)] to obtain 810 mg (94%) of the title compound.

$^1$H-NMR (400 MHz, CDCl$_3$) δ: 1.45 (3H, t, J=7.0 Hz), 3.83 (3H, s), 4.02 (2H, q, J=7.1 Hz), 4.10 (2H, s), 6.30 (1H, d, J=7.3 Hz), 7.56 (1H, d, J=11.6 Hz).

MS m/z: 214 [M+H]$^+$.

(23b)

4-Amino-2-ethoxy-5-fluorobenzoic Acid

[Formula 57]

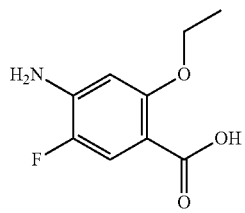

To a solution of the methyl 4-amino-2-ethoxy-5-fluorobenzoate (810 mg, 3.8 mmol) obtained in Example 23a in methanol (5 mL), a 1N sodium hydroxide solution (5 mL, 5 mmol) was added, followed by stirring at room temperature for 2 hours. Besides, a 4N potassium hydroxide solution (3 mL, 12 mmol) was added thereto, followed by stirring at room temperature for 12 hours. After completion of the reaction, a solid produced by adjusting the pH of the reaction solution to 3 with 1N hydrochloric acid and adding water (300 mL) was filtered and washed with water to obtain 630 mg (83%) of the title compound.

$^1$H-NMR (400 MHz, CD$_3$OD) δ: 1.44 (3H, t, J=7.0 Hz), 4.16 (2H, q, J=6.9 Hz), 6.48 (1H, d, J=7.3 Hz), 7.48 (1H, d, J=12.2 Hz).
MS m/z: 200 [M+H]$^+$.

(23c)

(−)-N-(4-Amino-2-ethoxy-5-fluorobenzoyl)-D-isovaline

[Formula 58]

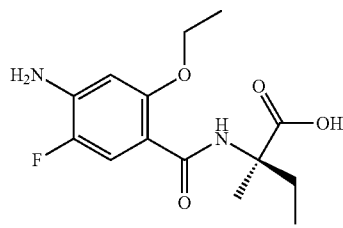

To a suspension of the 4-amino-2-ethoxy-5-fluorobenzoic acid (300 mg, 1.5 mmol) obtained in Example 23b, (R)-α-ethylalanine monohydrate (210 mg, 1.6 mol) and triethylamine (0.42 mL, 3.0 mmol) in DMF (1.5 mL), HATU (630 mg, 1.7 mmol) was added, followed by stirring at 50° C. for 5 hours. After completion of the reaction, the reaction solution was diluted with DMSO and purified by HPLC [elution solvent: 0.1% formic acid-containing aqueous solution/0.1% formic acid-containing acetonitrile=70/30-42/58 (V/V)] to obtain 180 mg (40%) of the title compound in the form of a solid. The thus obtained solid was crystalline.

$^1$H-NMR (400 MHz, CD$_3$OD) δ: 0.86 (3H, t, J=7.3 Hz), 1.51 (3H, t, J=7.0 Hz), 1.64 (3H, s), 1.88-1.97 (1H, m), 2.25-2.34 (1H, m), 4.14 (2H, q, J=7.1 Hz), 6.48 (1H, d, J=7.9 Hz), 7.52 (1H, d, J=12.8 Hz).
MS m/z: 299 [M+H]$^+$.
$[α]_D^{25}$ −22.71° (c 0.5, Methanol).

Figure 7:
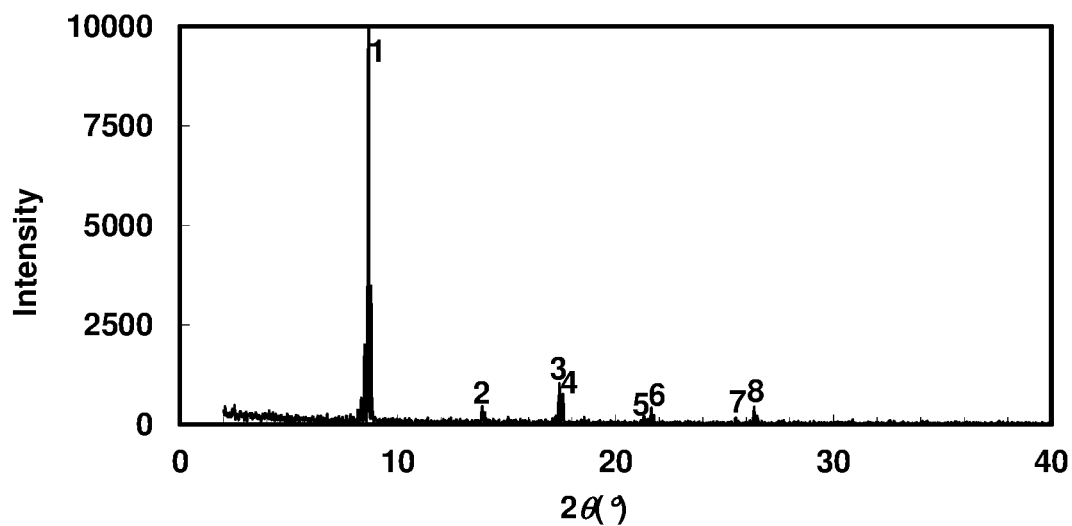
FIG. 7 is a powder X-ray diffraction diagram of crystals obtained in Example 23. The ordinate indicates diffraction intensity in count/sec. (cps), and the abscissa indicates a value of diffraction angle 2θ.

A powder X-ray diffraction pattern of the crystals obtained through irradiation with copper Kα radiation (λ=1.54 angstroms, scanning speed=20°/min) is illustrated in FIG. 7. Peaks each having relative intensity, calculated by assuming that the maximum peak intensity is 100, of 2 or more in FIG. 7 are shown in Table 7.

TABLE 7

| Peak No. | 2θ (°) | d Value (Å) | Relative Intensity | Peak No. | 2θ (°) | d Value (Å) | Relative Intensity |
|---|---|---|---|---|---|---|---|
| 1 | 8.64 | 10.23 | 100 | 5 | 21.30 | 4.17 | 2 |
| 2 | 13.86 | 6.38 | 5 | 6 | 21.62 | 4.11 | 4 |
| 3 | 17.40 | 5.09 | 10 | 7 | 25.52 | 3.49 | 2 |
| 4 | 17.58 | 5.04 | 9 | 8 | 26.34 | 3.38 | 4 |

(+)-N-(4-Amino-2-ethoxy-5-fluorobenzoyl)-L-isovaline

[Formula 59]

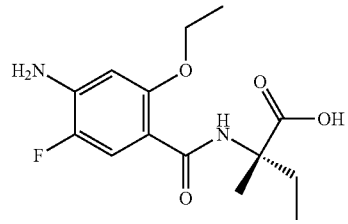

To a suspension of the 4-amino-2-ethoxy-5-fluorobenzoic acid (270 mg, 1.4 mmol) obtained in Example 23b, (S)-α-ethylalanine (190 mg, 1.6 mol) and triethylamine (0.38 mL, 2.7 mmol) in DMF (1.4 mL), HATU (570 mg, 1.5 mmol) was added, followed by stirring at 50° C. for 5 hours. After completion of the reaction, the reaction solution was diluted with DMSO and purified by HPLC [elution solvent: 0.1% formic acid-containing aqueous solution/0.1% formic acid-containing acetonitrile=65/35-37/63 (V/V)] to obtain 180 mg (45%) of the title compound in the form of a solid. The thus obtained solid was crystalline.

$^1$H-NMR (400 MHz, CD$_3$OD) δ: 0.86 (3H, t, J=7.3 Hz), 1.51 (3H, t, J=7.0 Hz), 1.64 (3H, s), 1.88-1.97 (1H, m), 2.25-2.34 (1H, m), 4.15 (2H, q, J=6.9 Hz), 6.49 (1H, d, J=7.3 Hz), 7.52 (1H, d, J=12.8 Hz).
MS m/z: 299 [M+H]$^+$.
$[α]_D^{25}$ +21.96° (c 0.5, Methanol).

Figure 8:
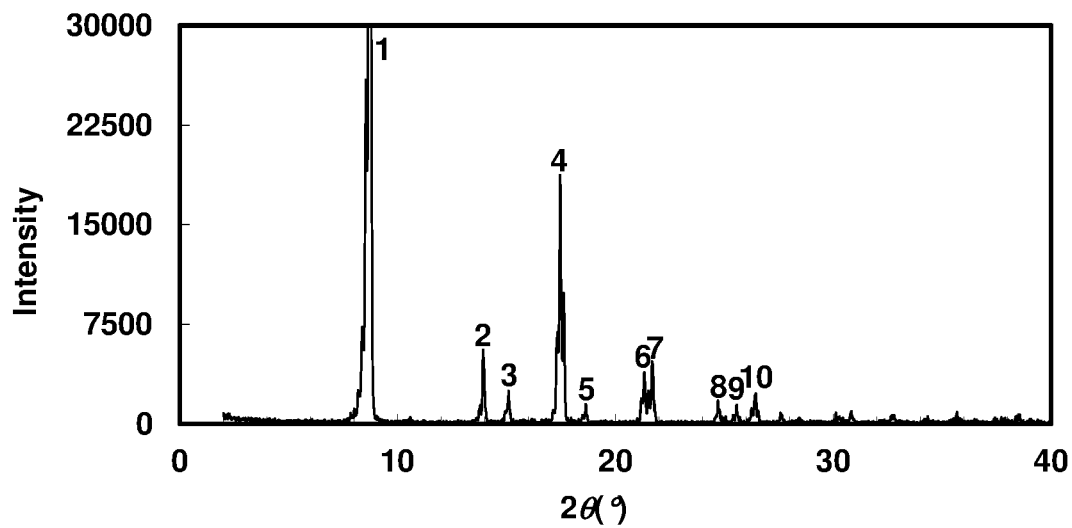
FIG. 8 is a powder X-ray diffraction diagram of crystals obtained in Example 24. The ordinate indicates diffraction intensity in count/sec. (cps), and the abscissa indicates a value of diffraction angle 2θ.

A powder X-ray diffraction pattern of the crystals obtained through irradiation with copper K radiation (λ=1.54 angstroms, scanning speed=20°/min) is illustrated in FIG. 8. Peaks each having relative intensity, calculated by assuming that the maximum peak intensity is 100, of 2 or more in FIG. 8 are shown in Table 8.

TABLE 8

| Peak No. | 2θ (°) | d Value (Å) | Relative Intensity | Peak No. | 2θ (°) | d Value (Å) | Relative Intensity |
|---|---|---|---|---|---|---|---|
| 1 | 8.72 | 10.13 | 100 | 6 | 21.32 | 4.16 | 4 |
| 2 | 13.94 | 6.35 | 6 | 7 | 21.70 | 4.09 | 5 |

47

TABLE 8-continued

| Peak No. | 2θ (°) | d Value (Å) | Relative Intensity | Peak No. | 2θ (°) | d Value (Å) | Relative Intensity |
|---|---|---|---|---|---|---|---|
| 3 | 15.08 | 5.87 | 3 | 8 | 24.72 | 3.60 | 2 |
| 4 | 17.46 | 5.08 | 16 | 9 | 25.56 | 3.48 | 2 |
| 5 | 18.64 | 4.76 | 2 | 10 | 26.42 | 3.37 | 3 |

Example 25

(−)-N-(4-Amino-5-chloro-2-propoxybenzoyl)-D-isovaline

[Formula 60]

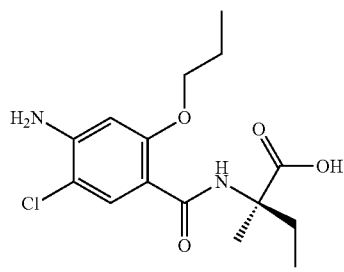

In the same manner as in Example 15, 160 mg (56%) of the title compound was obtained in the form of a solid from the 4-amino-5-chloro-2-propoxybenzoic acid (200 mg, 0.87 mmol) obtained in Example 14d and (R)-α-ethylalanine monohydrate (120 mg, 0.89 mmol). The thus obtained solid was crystalline.

$^1$H-NMR (400 MHz, CD$_3$OD) δ: 0.76 (3H, t, J=7.6 Hz), 0.96 (3H, t, J=7.3 Hz), 1.82-1.85 (3H, m), 2.19 (1H, td, J=14.3, 7.3 Hz), 3.95 (2H, t, J=6.4 Hz), 6.39 (1H, s), 7.70 (1H, s).

MS m/z: 329 [M+H]+.

[α]$_D^{25}$ −21.14° (c 0.5, Methanol).

Figure 9:
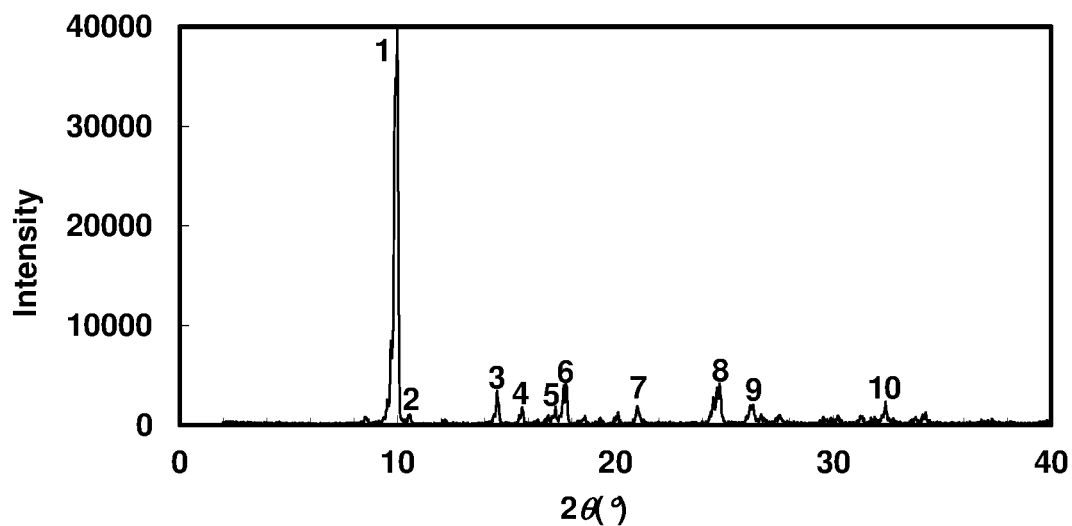
FIG. 9 is a powder X-ray diffraction diagram of crystals obtained in Example 25. The ordinate indicates diffraction intensity in count/sec. (cps), and the abscissa indicates a value of diffraction angle 2θ.

A powder X-ray diffraction pattern of the crystals obtained through irradiation with copper K radiation (λ=1.54 angstroms, scanning speed=20°/min) is illustrated in FIG. 9. Peaks each having relative intensity, calculated by assuming that the maximum peak intensity is 100, of 3 or more in FIG. 9 are shown in Table 9.

TABLE 9

| Peak No. | 2θ (°) | d Value (Å) | Relative Intensity | Peak No. | 2θ (°) | d Value (Å) | Relative Intensity |
|---|---|---|---|---|---|---|---|
| 1 | 9.94 | 8.89 | 100 | 6 | 17.70 | 5.01 | 10 |
| 2 | 10.54 | 8.39 | 3 | 7 | 21.02 | 4.22 | 5 |
| 3 | 14.58 | 6.07 | 7 | 8 | 24.76 | 3.59 | 9 |
| 4 | 15.72 | 5.63 | 4 | 9 | 26.26 | 3.39 | 5 |
| 5 | 17.22 | 5.15 | 4 | 10 | 32.38 | 2.76 | 5 |

48

Example 26

(−)-N-(4-Amino-2-methoxy-5-(trifluoromethyl)benzoyl)-D-isovaline

[Formula 61]

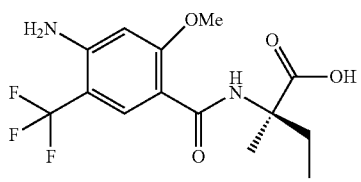

(26a)

Methyl 4-amino-2-methoxy-5-(trifluoromethyl)benzoate

[Formula 62]

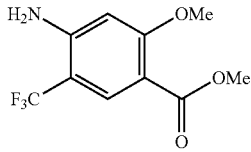

To a solution of (3,3-dimethyl-1-(trifluoromethyl)-1,2-benziodoxol (270 mg, 0.83 mmol) and chlorotris(trimethylsilyl)silane (47 mg, 0.17 mmol) in acetonitrile (2.2 mL), methyl 4-amino-2-methoxybenzoate (CAS Registry Number 27492-84-8) (100 mg, 0.55 mmol) was added, followed by stirring at 80° C. for 8 hours under a nitrogen atmosphere. After completion of the reaction, the reaction solution was cooled to room temperature and directly purified by silica gel column chromatography [elution solvent: n-hexane/ethyl acetate=70/30-0/100 (V/V)] to obtain 47 mg (34%) of the title compound.

$^1$H-NMR (400 MHz, CD$_3$OD) δ: 3.79 (3H, s), 3.84 (3H, s), 6.43 (1H, s), 7.93 (1H, s)

MS m/z: 250 [M+H]+.

(26b)

4-Amino-2-methoxy-5-(trifluoromethyl)benzoic Acid

[Formula 63]

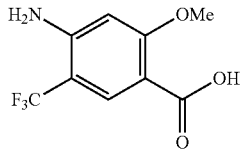

To a solution of the methyl 4-amino-2-methoxy-5-(trifluoromethyl)benzoate (47 mg, 0.19 mmol) obtained in Example 26a in methanol/THF (1/1, 4 mL), a 4N potassium hydroxide solution (0.5 mL, 2 mmol) was added, followed by stirring at room temperature for 6 hours. After completion of the reaction, a solid produced by adjusting the pH of the reaction solution to 3 with 2N hydrochloric acid was filtered and washed with water to obtain 36 mg (81%) of the title compound.

$^1$H-NMR (400 MHz, CD$_3$OD) δ: 3.89 (3H, s), 6.45 (1H, s), 8.01 (1H, s).

MS m/z: 236 [M+H]$^+$.

(26c)

(−)-N-(4-Amino-2-methoxy-5-(trifluoromethyl)benzoyl)-D-isovaline

[Formula 64]

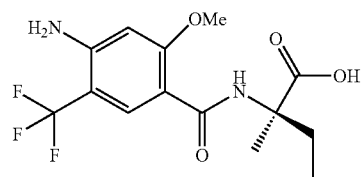

In the same manner as in Example 15, 30 mg (59%) of the title compound was obtained in the form of a solid from the 4-amino-2-methoxy-5-(trifluoromethyl)benzoic acid (36 mg, 0.15 mmol) obtained in Example 26b and (R)-α-ethylalanine monohydrate (22 mg, 0.16 mmol).

$^1$H-NMR (400 MHz, CD$_3$OD) δ: 0.84 (3H, t, J=7.3 Hz), 1.64 (3H, s), 1.87-1.96 (1H, m), 2.29-2.38 (1H, m), 3.99 (3H, s), 6.49 (1H, s), 8.06 (1H, s).

MS m/z: 335 [M+H]$^+$.

[α]$_D$ −16.80° (c 0.4, Methanol).

Example 27

(−)-N-(4-Amino-5-fluoro-2-propoxybenzoyl)-D-isovaline

[Formula 65]

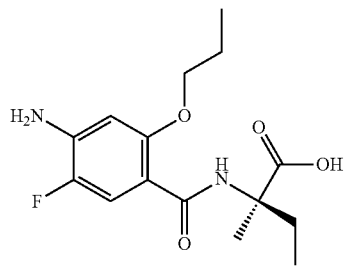

(27a)

Methyl 4-bromo-5-fluoro-2-propoxybenzoate

[Formula 66]

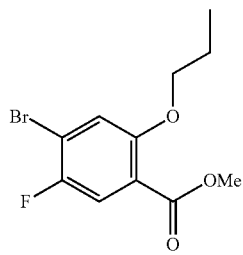

In the same manner as in Example 14a, 1.12 g (96%) of the title compound was obtained in the form of a solid from methyl 4-bromo-5-fluoro-2-hydroxybenzoate (CAS Registry Number 1193162-25-2) (1.0 g, 4.0 mmol), 1-iodopropane (0.59 mL, 6.0 mmol) and potassium carbonate (830 mg, 6.0 mmol).

$^1$H-NMR (400 MHz, CDCl$_3$) δ: 1.07 (3H, t, J=7.3 Hz), 1.81-1.90 (2H, m), 3.89 (3H, s), 3.96 (2H, t, J=6.4 Hz), 7.13 (1H, d, J=5.5 Hz), 7.58 (1H, d, J=8.5 Hz).

MS m/z: 291, 293 [M+H]$^+$.

(27b)

Methyl 4-amino-5-fluoro-2-propoxybenzoate

[Formula 67]

In the same manner as in Example 23a, 550 mg (62%) of the title compound was obtained from the methyl 4-bromo-5-fluoro-2-propoxybenzoate (1.1 g, 3.9 mmol) obtained in Example 27a, palladium acetate (879 mg, 0.39 mmol), 4,5-bis(diphenylphosphino)-9,9-dimethylxanthene (340 mg, 0.59 mmol), cesium carbonate (2.55 g, 7.8 mmol) and benzophenonimine (1.06 g, 5.9 mmol).

$^1$H-NMR (400 MHz, CDCl$_3$) δ: 1.07 (3H, t, J=7.3 Hz), 1.81-1.89 (2H, m), 3.83 (3H, s), 3.91 (2H, t, J=6.4 Hz), 4.09 (2H, s), 6.29 (1H, d, J=7.3 Hz), 7.56 (1H, d, J=12.2 Hz).

MS m/z: 228 [M+H]$^+$.

(27c)

4-Amino-5-fluoro-2-propoxybenzoic Acid

[Formula 68]

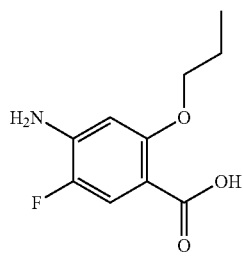

350 mg (83%) of the title compound was obtained in the form of a solid from the methyl 4-amino-5-fluoro-2-propoxybenzoate (450 mg, 2.0 mmol) obtained in Example 27b and a 4N sodium hydroxide solution (5 mL, 20 mmol).

$^1$H-NMR (400 MHz, CD$_3$OD) δ: 1.06 (3H, t, J=7.6 Hz), 1.81-1.90 (2H, m), 4.05 (2H, t, J=6.4 Hz), 6.48 (1H, d, J=7.3 Hz), 7.48 (1H, d, J=12.2 Hz).

MS m/z: 214 [M+H]$^+$.

(27d)

(−)-N-(4-Amino-5-fluoro-2-propoxybenzoyl)-D-isovaline

[Formula 69]

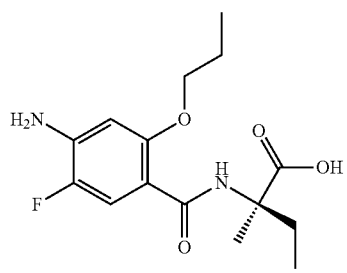

In the same manner as in Example 15, 170 mg (58%) of the title compound was obtained in the form of a solid from the 4-amino-5-fluoro-2-propoxybenzoic acid (200 mg, 0.94 mmol) obtained in Example 27b and (R)-α-ethylalanine monohydrate (130 mg, 0.96 mmol). The thus obtained solid was crystalline.

$^1$H-NMR (400 MHz, CD$_3$OD) δ: 0.86 (3H, t, J=7.3 Hz), 1.06 (3H, t, J=7.3 Hz), 1.63 (3H, s), 1.89-1.98 (3H, m), 2.24-2.33 (1H, m), 4.05 (2H, t, J=6.7 Hz), 6.48 (1H, d, J=7.3 Hz), 7.53 (1H, d, J=12.2 Hz), 8.85 (1H, br s).

MS m/z: 313 [M+H]$^+$.

$[α]_D^{25}$ −20.69° (c 0.5, Methanol).

Figure 10:
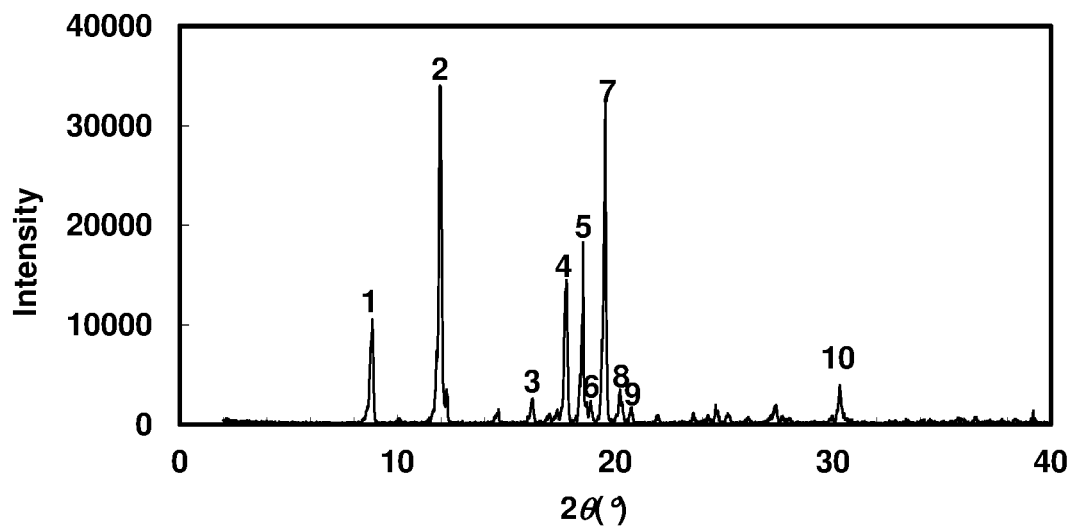
FIG. 10 is a powder X-ray diffraction diagram of crystals obtained in Example 27. The ordinate indicates diffraction intensity in count/sec. (cps), and the abscissa indicates a value of diffraction angle 2θ.

A powder X-ray diffraction pattern of the crystals obtained through irradiation with copper Kα radiation (λ=1.54 angstroms, scanning speed=20°/min) is illustrated in FIG. 10. Peaks each having relative intensity, calculated by assuming that the maximum peak intensity is 100, of 6 or more in FIG. 10 are shown in Table 10.

TABLE 10

| Peak No. | 2θ (°) | d Value (Å) | Relative Intensity | Peak No. | 2θ (°) | d Value (Å) | Relative Intensity |
|---|---|---|---|---|---|---|---|
| 1 | 8.82 | 10.02 | 28 | 6 | 18.88 | 4.70 | 6 |
| 2 | 11.96 | 7.39 | 100 | 7 | 19.52 | 4.54 | 84 |
| 3 | 16.18 | 5.47 | 8 | 8 | 20.22 | 4.39 | 10 |
| 4 | 17.72 | 5.00 | 40 | 9 | 20.72 | 4.28 | 6 |
| 5 | 18.50 | 4.79 | 41 | 10 | 30.30 | 2.95 | 10 |

Example 28

N-(4-Amino-2-methoxy-5-methylbenzoyl)-D-isovaline

[Formula 70]

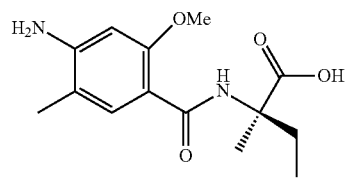

In the same manner as in Example 15, 9 mg (39%) of the title compound was obtained in the form of a solid from 4-amino-2-methoxy-5-methylbenzoic acid (CAS Registry Number 854645-44-6) (14 mg, 0.08 mmol) and (R)-α-ethylalanine monohydrate (11 mg, 0.08 mmol).

$^1$H-NMR (400 MHz, CD$_3$OD) δ: 0.85 (3H, t, J=7.6 Hz), 1.63 (3H, s), 1.87-1.96 (1H, m), 2.10 (3H, s), 2.25-2.33 (1H, m), 3.93 (3H, s), 6.45 (1H, s), 7.62 (1H, s).

MS m/z: 281 [M+H]$^+$.

Example 29

(−)-N-(4-Amino-5-cyano-2-ethoxybenzoyl)-D-isovaline

[Formula 71]

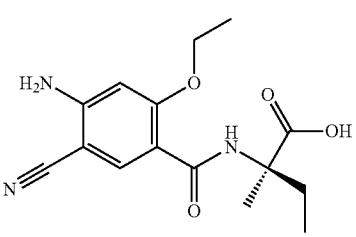

(29a)

4-Amino-5-cyano-2-methoxybenzoic Acid

[Formula 72]

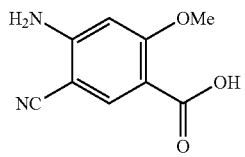

A suspension of 4-amino-5-bromo-2-ethoxybenzoic acid (280 mg, 1.1 mmol), 2-di-tert-butylphosphino-2',4',6'-triisopropylbiphenyl (46 mg, 0.11 mmol), [2-(di-tert-butylphosphino)-2',4',6'-triisopropyl-1,1'-biphenyl][2-(2-aminoethyl)phenyl]palladium(II) chloride (74 mg, 0.11 mmol), potassium acetate (320 mg, 3.2 mmol) and potassium hexacyanoferrate(II) trihydrate (1.4 g, 3.2 mmol) in 1,4-dioxane/water (11/2, 13 mL) was stirred at 110° C. for 2 hours under a nitrogen atmosphere. After completion of the reaction, the reaction solution was cooled to room temperature and filtered, and the filtrate was concentrated under reduced pressure. The thus obtained residue was purified by HPLC [elution solvent: 0.1% formic acid-containing aqueous solution/0.1% formic acid-containing acetonitrile=86/14-59/41 (V/V)] to obtain 95 mg (43%) of the title compound.

MS m/z: 207 [M+H]$^+$.

(29b)

(−)-N-(4-Amino-5-cyano-2-ethoxybenzoyl)-D-isovaline

[Formula 73]

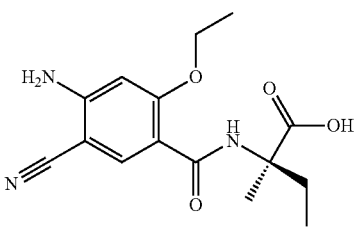

In the same manner as in Example 15, 100 mg (75%) of the title compound was obtained in the form of a solid from the 4-amino-5-cyano-2-methoxybenzoic acid (90 mg, 0.44 mmol) obtained in Example 29a and (R)-α-ethylalanine monohydrate (61 mg, 0.45 mmol).

$^1$H-NMR (400 MHz, CD$_3$OD) δ: 0.84 (3H, t, J=7.3 Hz), 1.54 (3H, t, J=7.0 Hz), 1.64 (3H, s), 1.87-1.96 (1H, m), 2.28-2.37 (1H, m), 4.21 (2H, q, J=6.9 Hz), 6.43 (1H, s), 7.98 (1H, s).

MS m/z: 306 [M+H]$^+$.

[α]$_D^{25}$ −26.77° (c 0.5, Methanol).

Example 30

(−)-N-(4-Amino-5-fluoro-2-methoxybenzoyl)-D-isovaline

[Formula 74]

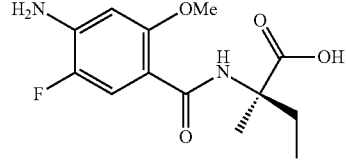

In the same manner as in Example 15, 220 mg (49%) of the title compound was obtained in the form of a solid from 4-amino-5-fluoro-2-methoxybenzoic acid (CAS Registry Number 1346763-78-7) (290 mg, 1.6 mmol) and (R)-α-ethylalanine monohydrate (220 mg, 1.6 mmol).

$^1$H-NMR (400 MHz, CD$_3$OD) δ: 0.84 (3H, t, J=7.3 Hz), 1.63 (3H, s), 1.91 (1H, dd, J=14.0, 7.3 Hz), 2.31 (1H, dd, J=14.0, 7.3 Hz), 3.94 (3H, s), 6.50 (1H, d, J=7.3 Hz), 7.52 (1H, d, J=12.1 Hz), 8.96 (1H, s).

MS m/z: 285 [M+H]$^+$.

[α]$_D^{25}$ −18.93° (c 0.5, Methanol).

Example 31

(−)-N-[4-Amino-5-chloro-2-(difluoromethoxy)benzoyl]-D-isovaline

[Formula 75]

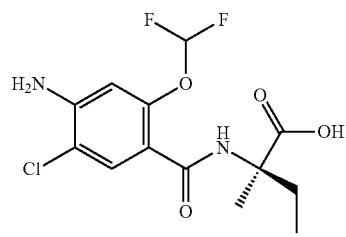

(31a)

4-Amino-5-chloro-(2-difluoromethoxy)benzoic Acid

[Formula 76]

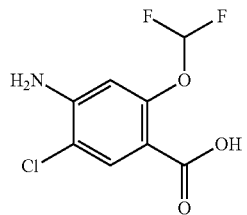

In the same manner as in Examples 14c and 14d, 40 mg (28%) of the title compound was obtained in the form of a solid from methyl 4-amino-2-(difluoromethoxy)benzoate (CAS Registry Number 632626-84-7) (130 mg, 0.6 mmol), Palau' Chlor (registered trademark, 130 mg, 0.6 mmol) and a 4N sodium hydroxide solution (1.5 mL, 6 mmol).
MS m/z: 238 [M+H]$^+$.

(31b)

(−)-N-[4-Amino-5-chloro-2-(difluoromethoxy)benzoyl]-D-isovaline

[Formula 77]

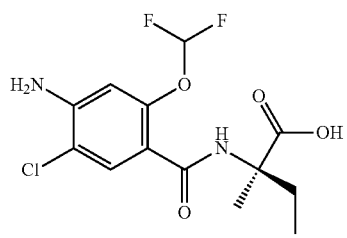

In the same manner as in Example 15, 18 mg (34%) of the title compound was obtained in the form of a solid from the 4-amino-5-chloro-(2-difluoromethoxy)benzoic acid (37 mg, 0.16 mmol) obtained in Example 31a and (R)-α-ethylalanine monohydrate (22 mg, 0.16 mmol).

$^1$H-NMR (400 MHz, CD$_3$OD) δ: 0.88 (3H, t, J=7.6 Hz), 1.60 (3H, s), 1.94 (1H, td, J=14.3, 7.1 Hz), 2.18 (1H, td, J=14.5, 7.1 Hz), 6.61 (1H, s), 6.89 (1H, t, J=72.9 Hz), 7.73 (1H, s).
MS m/z: 337 [M+H]$^+$.
$[\alpha]_D^{25}$ −14.44° (c 0.5, Methanol).

Example 32

N-(4-Amino-5-fluoro-2-propoxybenzoyl)-2-methylalanine

[Formula 78]

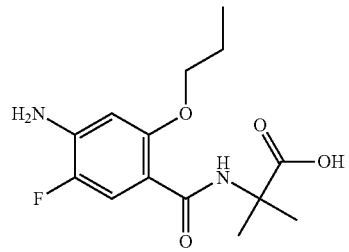

In the same manner as in Example 15, 120 mg (57%) of the title compound was obtained in the form of a solid from the 4-amino-5-fluoro-2-propoxybenzoic acid (150 mg, 0.70 mmol) obtained in Example 27c and methyl 2-methylalanine hydrochloride (130 mg, 0.84 mmol).

$^1$H-NMR (400 MHz, CD$_3$OD) δ: 1.09 (3H, t, J=7.3 Hz), 1.60 (6H, s), 1.91-1.94 (2H, m), 4.05 (2H, t, J=6.4 Hz), 6.49 (1H, d, J=7.3 Hz), 7.52 (1H, d, J=12.8 Hz).
MS m/z: 299 [M+H]$^+$.

(Test Example 1) Tryptophanase Enzyme Inhibitory Activity

Tryptophanase inhibitory activity was evaluated by a method using lactate dehydrogenase (LDH). The reaction time-dependent reduction in NADH conjugated with the enzymatic reaction, with LDH, of pyruvic acid produced through the enzymatic reaction of L-tryptophan as a substrate with tryptophanase, was measured with a spectrophotometer (Phillips-R S et al., Biochemistry, 23, 6228-6234 (1984)). Enzyme inhibitory activity obtained without adding a test compound (by adding DMSO alone) in the presence of tryptophanase was used as a control. As the enzyme, tryptophanase of *Bacteroides tetaiotaomicron* (Genbank accession number: HC914434.1) was used.

A test compound solution was prepared by dissolving each test compound in DMSO at concentrations (from 30 mM to 30 nM at 10-fold common ratio). LDH, NADH and L-tryptophan were dissolved, using distilled water, respectively to concentrations of 80 units/mL, 10 mM and 50 mM. *Bacteroides* tryptophanase was prepared to 30 mg/mL. A potassium phosphate buffer was used as the buffer. Compositions of reaction solutions are shown in Table 11.

TABLE 11

| Composition of Reaction Solution | Concentration | Final Concentration | Reaction Solution | | |
|---|---|---|---|---|---|
| | | | Reaction Solution A | Reaction Solution B | Reaction Solution C |
| Distilled Water | — | — | | | |
| KPB (pH8.3) | 1M | 125 mM | | | |
| LDH | 80 units/mL | 2.5 units/mL | A | B | C |
| NADH | 10 mM | 0.3125 mM | | | |
| Bacteroides Tryptophanase | 30 mg/mL | 0.015 mg/mL | | | |
| Test Compound Solution | Arbitrary Concentration | 1/100 of Preparation Concentration | | | |
| L-Tryptophan | 50 mM | 10 mM | | | |

A reaction solution A was dispensed at 284.8 μL per well into a 96-well plate, and the test compound solution was added at 3.2 μL per well to obtain a final concentration of 1/100 (reaction solution B). The reaction solution B was incubated at 37° C. for 30 minutes, L-tryptophan was added thereto at 32 μL per well to obtain a final concentration of 10 mM (reaction solution C), and the enzyme reaction was performed at 37° C. over 30 minutes with absorbance at 340 nm measured for monitoring the NADH loss. Based on the NADH loss, the tryptophanase inhibitory activity of the compound was evaluated.

Inhibitory activities (IC50, μM) of these test compounds are shown in Table 12.

TABLE 12

| Test Compound | Bacteroides Tryptophanase Inhibitory Activity (IC50, μM) |
| --- | --- |
| Compound of Example 1 | 27.1 |
| Compound of Example 2 | 7.8 |
| Compound of Example 3 | 8.0 |
| Compound of Example 4 | 1.7 |
| Compound of Example 5 | 1.0 |
| Compound of Example 6 | 0.2 |
| Compound of Example 7 | 6.9 |
| Compound of Example 8 | 1.3 |
| Compound of Example 9 | 0.39 |
| Compound of Example 10 | 1.53 |
| Compound of Example 11 | 0.09 |
| Compound of Example 12 | 0.31 |
| Compound of Example 13 | 0.08 |
| Compound of Example 14 | 0.20 |
| Compound of Example 15 | 0.77 |
| Compound of Example 16 | 0.36 |
| Compound of Example 17 | 0.14 |
| Compound of Example 18 | 0.10 |
| Compound of Example 19 | 0.06 |
| Compound of Example 20 | 0.05 |
| Compound of Example 21 | 0.10 |
| Compound of Example 22 | 0.08 |
| Compound of Example 23 | 0.49 |
| Compound of Example 24 | 0.13 |
| Compound of Example 25 | 0.04 |
| Compound of Example 26 | 0.84 |
| Compound of Example 27 | 0.09 |
| Compound of Example 28 | 3.13 |
| Compound of Example 29 | 0.02 |
| Compound of Example 30 | 5.61 |
| Compound of Example 31 | 0.11 |
| Compound of Example 32 | 0.54 |

In this manner, the compounds of the present invention exhibit excellent tryptophanase inhibitory activity, and are useful as pharmaceuticals as an agent for reducing indoxyl sulfate in the blood, an agent for preventing or treating a disease caused by an increase in indoxyl sulfate in the blood, an agent for delaying transition to renal replacement therapy in a patient with chronic kidney disease at pre-dialysis stage, and an agent for suppressing worsening of residual renal function in a patient after transition to renal replacement therapy.

(Test Example 2) Indole Production Suppressing Effect

The effect of a tryptophanase inhibitory compound to suppress indole production from a viable bacterium can be evaluated through the following operation.

When *E. coli* (*Eschelicia coli*) is used as a strain known to produce indole, the strain is cultured in an LB medium at 37° C. for 12 to 18 hours under anaerobic conditions, and then, suspended in an assay medium (5 mM L-Tryptophan/PBS(+)/25 mM HEPES (pH8)) in such a manner as to obtain O.D. of about 0.3. When *bacteroides* is used, the strain is cultured in a modified GAM medium at 37° C. for 12 to 18 hours under anaerobic conditions, and then suspended in an assay medium (5 mM L-Tryptophan/PBS(+)/25 mM HEPES (pH8)) in such a manner as to obtain O.D. of about 1.1. The thus obtained viable bacterial suspension prepared to have a final concentration of a compound of 1 μM to 10 mM is dispensed at 200 μL per well into a 96-well plate and cultured at 37° C. for 2 to 4 hours under anaerobic conditions, O.D., an ATP concentration (that can be quantitatively determined by using BacTiter-Glo (Promega Corporation)) and an indole concentration in the culture supernatant (that can be quantitatively determined by utilizing Ehrlich reaction) are measured. The effect of the tryptophanase inhibitory compound to suppress indole production from a viable bacterium can be evaluated depending on the degree of lowering of the indole concentration in the culture supernatant. It can be checked whether or not the effect is derived from a function other than tryptophanase inhibition, such as a bactericidal function or a bacterial growth inhibitory function, depending on lowering of the O.D. or reduction in the ATP concentration or by performing a generally practiced antibacterial activity test (a MIC (minimum growth inhibition concentration) test) using levofloxacin or the like as a positive control.

The activities of inhibiting indole production of the compounds of the respective examples shown in Table 13 were measured by the above-described method using *Bacteroides* to evaluate the effect of inhibiting indole production. The results are shown in Table 13.

TABLE 13

| Test Compound | Bacteroides Indole Production Inhibitory Activity(IC50, μM) |
| --- | --- |
| Compound of Example 6 | <3.0 |
| Compound of Example 10 | <3.0 |
| Compound of Example 11 | <3.0 |
| Compound of Example 15 | <3.0 |
| Compound of Example 16 | <3.0 |
| Compound of Example 21 | <3.0 |
| Compound of Example 23 | <3.0 |
| Compound of Example 24 | <3.0 |
| Compound of Example 25 | <3.0 |
| Compound of Example 27 | <3.0 |

In this manner, the compounds of the present invention exhibited excellent activity of inhibiting indole production. Accordingly, the compounds of the present invention are useful as pharmaceuticals as an agent for reducing indoxyl sulfate in the blood, an agent for preventing or treating a disease caused by an increase in indoxyl sulfate in the blood, an agent for delaying transition to renal replacement therapy in a patient with chronic kidney disease at pre-dialysis stage, and an agent for suppressing worsening of residual renal function in a patient after transition to renal replacement therapy.

(Test Example 3) Effect of Reducing Plasma Indoxyl Sulfate Concentration in Mice An effect of a tryptophanase inhibitory compound to reduce plasma indoxyl sulfate concentration in a mouse can be evaluated through the following operation.

After fasting male BALB/c mice overnight, a tryptophanase inhibitory compound dissolved or suspended at a concentration of 0.01 to 10 mg/mL in 0.5% methylcellulose (MC) solution used as a solvent and 0.5% MC solution are orally administered by gavage at a volume of 10 mL/kg respectively to test compound groups and to a solvent control group. 30 minutes after the administration of the test compound or the solvent, L-tryptophan, that is, a substrate of tryptophanase, is orally administered by gavage at a dose of 1 to 3 g/kg. The L-tryptophan is suspended in a 0.5% tragacanth solution. For 12 hours after the administration of the L-tryptophan, blood is collected over time from a tail vein by using a hematocrit tube. The thus obtained blood is centrifuged at 11,000 rpm for 5 minutes to collect plasma, and the indoxyl sulfate concentration in the plasma is measured singly by liquid chromatography (fluorescence detection) or its combination with a mass spectrometer used subsequently. Plasma indoxyl sulfate concentration in the test compound group against the plasma indoxyl sulfate concentration in the solvent control group is calculated as, for example, a ratio of the area under a curve of the indoxyl sulfate concentration, and thus, the efficacy of each compound in vivo can be compared.

The indoxyl sulfate concentrations in plasma obtained by using the compounds of the respective examples shown in Table 14 below were measured by the above-described method to evaluate the plasma indoxyl sulfate suppressing effect. The results are shown in Table 14.

TABLE 14

| Test Compound | Plasma Indoxyl Sulfate Reduction Effect in Male BALB/c Mouse (Indoxyl sulfate reduction effect in plasma 6 hours after administration of L-tryptophan: ED75-, mg/kg) |
|---|---|
| Compound of Example 6 | 1 |
| Compound of Example 10 | 1 |
| Compound of Example 11 | 1 |
| Compound of Example 15 | 1 |
| Compound of Example 16 | 1 |
| Compound of Example 21 | 1 |
| Compound of Example 23 | 1 |
| Compound of Example 24 | 1 |
| Compound of Example 25 | 1 |
| Compound of Example 27 | 1 |

In this manner, the compounds of the present invention exhibited an excellent indoxyl sulfate-reducing function in plasma. Accordingly, the compounds of the present invention are useful as pharmaceuticals as an agent for reducing indoxyl sulfate in the blood, an agent for preventing or treating a disease caused by an increase in indoxyl sulfate in the blood, an agent for delaying transition to renal replacement therapy in a patient with chronic kidney disease at pre-dialysis stage, and an agent for suppressing worsening of residual renal function in a patient after transition to renal replacement therapy.

(Formulation Example 1) Hard Capsule

A unit capsule was produced by filling each standard two-part hard gelatin capsule with 100 mg of the compound of Example 1 in the form of a powder, 150 mg of lactose, 50 mg of cellulose and 6 mg of magnesium stearate, and the resultant capsule was washed and then dried.

(Formulation Example 2) Soft Capsule

A soft capsule containing 100 mg of an active component was obtained by preparing a mixture of the compound of Example 2 in digestible oil such as soybean oil, cottonseed oil or olive oil and injecting the resultant into gelatin by using a positive displacement pump, and the resultant capsule was washed and then dried.

(Formulation Example 3) Tablet

A tablet was produced by an ordinary method using 100 mg of the compound of Example 3, 0.2 mg of colloidal silicon dioxide, 5 mg of magnesium stearate, 275 mg of microcrystalline cellulose, 11 mg of starch and 98.8 mg of lactose.

The resultant tablet may be coated with a coating if desired.

(Formulation Example 4) Suspension

A suspension containing, in 5 mL, 100 mg of the compound of Example 4 in the form of a fine powder, 100 mg of sodium carboxymethylcellulose, 5 mg of sodium benzoate, 1.0 g of a sorbitol solution (The Japanese Pharmacopoeia) and 0.025 mL of vanillin was produced.

INDUSTRIAL APPLICABILITY

The inventive compound (I) or a pharmacologically acceptable salt thereof, or a crystalline form thereof, has an excellent tryptophanase inhibitory effect, and exhibits an effect of reducing indoxyl sulfate in the blood and suppressing worsening of renal function. Accordingly, the compounds of the present invention are useful as an agent for reducing indoxyl sulfate in the blood, an agent for preventing or treating a disease caused by an increase in indoxyl sulfate in the blood, an agent for delaying transition to renal replacement therapy in a patient with chronic kidney disease (CKD) at pre-dialysis stage, and an agent for suppressing worsening of residual renal function in a patient after transition to renal replacement therapy.

The invention claimed is:

1. A pharmaceutical composition comprising, as an active ingredient, a compound represented by formula (I) or a pharmacologically acceptable salt thereof:

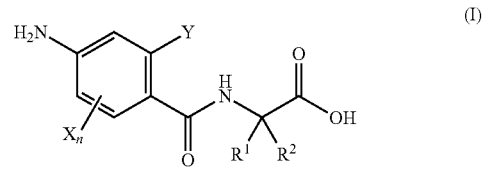

wherein $R^1$ and $R^2$ are the same or different, and represent a C1-C6 alkyl group, a halogeno C1-C6 alkyl group or a C3-C6 cycloalkyl group; n represents 0, 1 or 2; each X is the same or different, and represents a C1-C6 alkyl group, a C3-C6 cycloalkyl group, a halogen atom, a cyano group, a halogeno C1-C6 alkyl group, a C1-C6 alkoxy group, a halogeno C1-C6 alkoxy group or a C3-C6 cycloalkoxy group; and Y represents a hydrogen atom, a C1-C6 alkoxy group, a C3-C6 cycloalkoxy group or a halogeno C1-C6 alkoxy group.

2. A compound represented by formula (Ia) or a pharmacologically acceptable salt thereof:

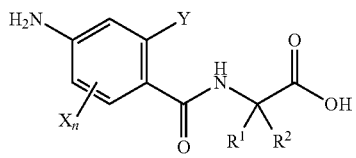

wherein
(A) $R^1$ and $R^2$ are the same or different, and represent a $C_1$-$C_6$ alkyl group, a halogeno $C_1$-$C_6$ alkyl group or a $C_3$-$C_6$ cycloalkyl group; n represents 1; X represents a $C_1$-$C_6$ alkyl group, a $C_3$-$C_6$ cycloalkyl group, a halogen atom, a cyano group, a halogeno $C_1$-$C_6$ alkyl group, a $C_1$-$C_6$ alkoxy group, a halogeno $C_1$-$C_6$ alkoxy group or a $C_3$-$C_6$ cycloalkoxy group; and Y represents a $C_1$-$C_6$ alkoxy group, a $C_3$-$C_6$ cycloalkoxy group or a halogeno $C_1$-$C_6$ alkoxy group; or
(B) $R^1$ represents an ethyl group; $R^2$ represents a $C_1$-$C_6$ alkyl group, a halogeno $C_1$-$C_6$ alkyl group or a $C_3$-$C_6$ cycloalkyl group; n represents 0, 1 or 2; X represents a $C_1$-$C_6$ alkyl group, a $C_3$-$C_6$ cycloalkyl group, a halogen atom, a cyano group, a halogeno $C_1$-$C_6$ alkyl group, a $C_1$-$C_6$ alkoxy group or a halogeno $C_1$-$C_6$ alkoxy group; and Y represents a hydrogen atom, provided that X does not represent a halogen atom or a $C_1$-$C_6$ alkoxy group when $R^2$ represents an ethyl group; and neither X represents a $C_1$-$C_6$ alkoxy group when n represents 2.

3. The compound according to claim 2 represented by formula (I-1) or a pharmacologically acceptable salt thereof:

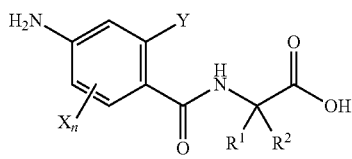

wherein $R^1$ and $R^2$ are the same or different, and represent a $C_1$-$C_4$ alkyl group or a $C_3$-$C_4$ cycloalkyl group; n represents 1; X represents a $C_1$-$C_4$ alkyl group, a $C_3$-$C_4$ cycloalkyl group, a halogen atom, a cyano group or a halogeno $C_1$-$C_4$ alkyl group; and Y represents a $C_1$-$C_4$ alkoxy group or a halogeno $C_1$-$C_4$ alkoxy group.

4. The compound according to claim 3 represented by formula (I-1a) or a pharmacologically acceptable salt thereof:

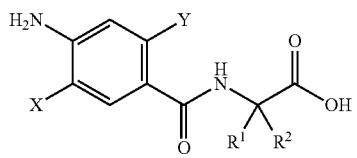

wherein $R^1$ and $R^2$ are the same or different, and represent a $C_1$-$C_3$ alkyl group or a cyclopropyl group; X represents a $C_1$-$C_3$ alkyl group, a fluorine atom, a chlorine atom, a bromine atom, an iodine atom, a cyano group or a fluoro-$C_1$-$C_3$ alkyl group; and Y represents a $C_1$-$C_3$ alkoxy group or a fluoro-$C_1$-$C_3$ alkoxy group.

5. The compound according to claim 4, or a pharmacologically acceptable salt thereof, wherein $R^1$ and $R^2$ are the same or different, and represent a methyl group, an ethyl group, a propyl group or a cyclopropyl group.

6. The compound according to claim 4, or a pharmacologically acceptable salt thereof, wherein $R^1$ and $R^2$ are the same or different, and represent a methyl group or an ethyl group.

7. The compound according to claim 4, or a pharmacologically acceptable salt thereof, wherein X represents a fluorine atom, a chlorine atom, a bromine atom or an iodine atom.

8. The compound according to claim 4, or a pharmacologically acceptable salt thereof, wherein X represents a fluorine atom or a chlorine atom.

9. The compound according to claim 4, or a pharmacologically acceptable salt thereof, wherein Y represents a methoxy group, an ethoxy group or a propoxy group.

10. The compound according to claim 2 represented by formula (I-2) or a pharmacologically acceptable salt thereof:

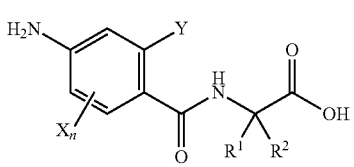

wherein $R^1$ represents an ethyl group; $R^2$ represents a $C_1$-$C_4$ alkyl group or a $C_3$-$C_4$ cycloalkyl group; n represents 0, 1 or 2; each X is the same or different, and represents a $C_1$-$C_4$ alkyl group, a $C_3$-$C_4$ cycloalkyl group, a halogen atom, a cyano group or a halogeno $C_1$-$C_4$ alkyl group; and Y represents a hydrogen atom, provided that X does not represent a halogen atom or a $C_1$-$C_4$ alkoxy group when $R^2$ represents an ethyl group, and neither X represents a $C_1$-$C_4$ alkoxy group when n represents 2.

11. The compound according to claim 10 represented by formula (I-2a) or a pharmacologically acceptable salt thereof:

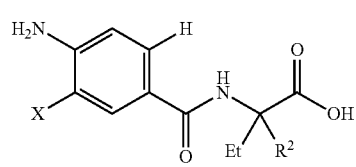

wherein $R^2$ represents a $C_1$-$C_3$ alkyl group or a cyclopropyl group; X represents a $C_1$-$C_3$ alkyl group, a fluorine atom, a chlorine atom or a bromine atom, provided that X does not represent a fluorine atom, a chlorine atom or a bromine atom when $R^2$ represents an ethyl group.

12. The compound according to claim 11, or a pharmacologically acceptable salt thereof, wherein $R^2$ represents a methyl group, an ethyl group or a cyclopropyl group.

13. The compound according to claim 11, or a pharmacologically acceptable salt thereof, wherein X represents a methyl group or a chlorine atom.

14. The compound according to claim 2, selected from the group consisting of 2-[(4-amino-5-chloro-2-methoxybenzoyl)amino]-2-ethylbutanoic acid, (−)-N-(4-amino-5-fluoro-2-propoxybenzoyl)-D-isovaline, (+)-N-(4-amino-5-chloro-2-methoxybenzoyl)-L-isovaline, (−)-N-(4-amino-5-chloro-2-methoxybenzoyl)-D-isovaline, (+)-N-(4-amino-5-chloro-2-ethoxybenzoyl)-L-isovaline, (−)-N-(4-amino-5-chloro-2-ethoxybenzoyl)-D-isovaline, (−)-N-(4-amino-5-chloro-2-propoxybenzoyl)-D-isovaline, (+)-N-(4-amino-5-bromo-2-methoxybenzoyl)-L-isovaline, (−)-N-(4-amino-5-bromo-2-methoxybenzoyl)-D-isovaline, (+)-N-(4-amino-5-bromo-2-ethoxybenzoyl)-L-isovaline, (−)-N-(4-amino-5-bromo-2-ethoxybenzoyl)-D-isovaline, (+)-N-(4-amino-5-iodo-2-methoxybenzoyl)-L-isovaline, (−)-N-(4-amino-5-iodo-2-methoxybenzoyl)-D-isovaline, (+)-N-(4-amino-2-ethoxy-5-fluorobenzoyl)-L-isovaline, (−)-N-(4-amino-2-ethoxy-5-fluorobenzoyl)-D-isovaline, (+)-N-(4-amino-2-ethoxy-5-iodobenzoyl)-L-isovaline, and (−)-N-(4-amino-2-ethoxy-5-iodobenzoyl)-D-isovaline;

or a pharmacologically acceptable salt thereof.

15. A pharmaceutical composition comprising, as an active ingredient, the compound according to claim 2 or a pharmacologically acceptable salt thereof.

16. A crystalline form of the compound according to claim 2, selected from the group consisting of:

crystalline 2-[(4-amino-5-chloro-2-methoxybenzoyl)amino]-2-ethylbutanoic acid having characteristic peaks at interplanar spacings d of 7.51, 7.33, 6.67, 6.15, 5.32, 5.24, 4.98, 4.79, 3.96 and 3.59 angstroms;

crystalline (−)-N-(4-amino-5-fluoro-2-propoxybenzoyl)-D-isovaline having characteristic peaks at interplanar spacings d of 10.02, 7.39, 5.47, 5.00, 4.79, 4.70, 4.54, 4.39, 4.28 and 2.95 angstroms;

crystalline (−)-N-(4-amino-5-chloro-2-methoxybenzoyl)-D-isovaline having characteristic peaks at interplanar spacings d of 6.61, 5.96, 5.16, 5.10, 4.85, 4.68, 4.50, 4.08, 3.43 and 2.69 angstroms;

crystalline (−)-N-(4-amino-5-chloro-2-ethoxybenzoyl)-D-isovaline having characteristic peaks at interplanar spacings d of 10.67, 10.06, 5.33, 5.09, 5.02, 4.26, 4.14, 3.67, 3.47 and 2.96 angstroms;

crystalline (−)-N-(4-amino-5-chloro-2-propoxybenzoyl)-D-isovaline having characteristic peaks at interplanar spacings d of 8.89, 8.39, 6.07, 5.63, 5.15, 5.01, 4.22, 3.59, 3.39 and 2.76 angstroms;

crystalline (−)-N-(4-amino-5-bromo-2-methoxybenzoyl)-D-isovaline having characteristic peaks at interplanar spacings d of 10.37, 9.40, 6.12, 5.17, 4.87, 4.20, 3.89, 3.45, 3.05 and 2.84 angstroms;

crystalline (−)-N-(4-amino-5-bromo-2-ethoxybenzoyl)-D-isovaline having characteristic peaks at interplanar spacings d of 10.23, 6.38, 5.09, 5.04, 4.17, 4.11, 3.49 and 3.38 angstroms;

crystalline (−)-N-(4-amino-5-iodo-2-methoxybenzoyl)-D-isovaline having characteristic peaks at interplanar spacings d of 12.00, 5.99, 5.53, 5.17, 5.08, 3.68, 3.35, 3.06, 2.86 and 2.39 angstroms;

crystalline (+)-N-(4-amino-2-ethoxy-5-fluorobenzoyl)-L-isovaline having characteristic peaks at interplanar spacings d of 10.13, 6.35, 5.87, 5.08, 4.76, 4.16, 4.09, 3.60, 3.48 and 3.37 angstroms; and crystalline (−)-N-(4-amino-2-ethoxy-5-fluorobenzoyl)-D-isovaline having characteristic peaks at interplanar spacings d of 10.23, 6.38, 5.09, 5.04, 4.17, 4.11, 3.49 and 3.38 angstroms;

all in powder X-ray diffraction obtained through irradiation with copper Kα radiation (wavelength λ=1.54 angstroms).

17. A pharmaceutical composition comprising, as an active ingredient, any one of the crystalline forms of the compound according to claim 16.

18. A method for reducing indoxyl sulfate in the blood, comprising administering, to a mammal, an effective dose of the compound according to claim 2 or a pharmacologically acceptable salt thereof.

19. The method according to claim 18, wherein the mammal is a human.

20. A method for reducing indoxyl sulfate in the blood, comprising administering, to a mammal, an effective dose of the compound according to a crystalline form of the compound according to claim 16.

21. The method according to claim 20, wherein the mammal is a human.

* * * * *